United States Patent
Kandori

(10) Patent No.: US 10,502,713 B2
(45) Date of Patent: Dec. 10, 2019

(54) ULTRASOUND PROBE AND INFORMATION ACQUISITION DEVICE INCLUDING ULTRASOUND PROBE

(71) Applicant: CANON KABUSHIKI KAISHA, Tokyo (JP)

(72) Inventor: Atsushi Kandori, Ebina (JP)

(73) Assignee: Canon Kabushiki Kaisha, Tokyo (JP)

( * ) Notice: Subject to any disclaimer, the term of this patent is extended or adjusted under 35 U.S.C. 154(b) by 731 days.

(21) Appl. No.: 14/950,187

(22) Filed: Nov. 24, 2015

(65) Prior Publication Data
US 2016/0153940 A1   Jun. 2, 2016

(30) Foreign Application Priority Data
Nov. 28, 2014   (WO) .................. PCT/JP2014/081520

(51) Int. Cl.
*G01N 29/24*   (2006.01)
*A61B 5/00*   (2006.01)

(52) U.S. Cl.
CPC ....... *G01N 29/2406* (2013.01); *A61B 5/0095* (2013.01); *G01N 29/2418* (2013.01)

(58) Field of Classification Search
CPC ........... G01N 29/2406; G01N 29/2418; G01N 29/06; A61B 5/0095; A61B 5/4312; A61B 5/0091
See application file for complete search history.

(56) References Cited

U.S. PATENT DOCUMENTS

| | | | | |
|---|---|---|---|---|
| 5,713,356 | A * | 2/1998 | Kruger | A61B 5/0091 600/407 |
| 6,216,025 | B1 * | 4/2001 | Kruger | A61B 5/0095 128/915 |
| 6,419,648 | B1 * | 7/2002 | Vitek | A61N 7/02 601/3 |
| 2006/0184072 | A1 * | 8/2006 | Manna | A61N 7/02 601/2 |

(Continued)

FOREIGN PATENT DOCUMENTS

| JP | H07171152 A | 7/1995 |
|---|---|---|
| JP | 2009278054 A | 11/2009 |

(Continued)

*Primary Examiner* — Helen C Kwok
(74) *Attorney, Agent, or Firm* — Canon U.S.A., Inc. IP Division

(57) ABSTRACT

An ultrasound probe to detect photoacoustic waves (ultrasound waves) over a wide frequency band with excellent sensitivity by providing electrostatic capacitance type transducers having a characteristic of being able to receive photoacoustic waves (ultrasound waves) over a wide frequency range in a plurality of flat surface parts on an inner wall surface of a supporting member having a spherical surface. The ultrasound probe includes electrostatic capacitance type transducers with each transducer including a vibration film which includes a first electrode and a second electrode which is provided with a space between the vibration film and the second electrode, and a supporting member that has a curved surface on which the plurality of transducers are provided. An inner wall surface of the supporting member includes a plurality of flat surface parts, and the transducers are provided on the flat surface parts with plate-like substrates therebetween.

21 Claims, 16 Drawing Sheets

(56) References Cited

U.S. PATENT DOCUMENTS

| | | | |
|---|---|---|---|
| 2008/0262357 A1* | 10/2008 | Wodnicki | G01S 7/52017 600/459 |
| 2008/0304729 A1* | 12/2008 | Peszynski | A61B 8/4236 382/131 |
| 2009/0182229 A1* | 7/2009 | Wodnicki | B06B 1/0622 600/437 |
| 2010/0207484 A1* | 8/2010 | Chang | B06B 1/0292 310/300 |
| 2011/0071396 A1* | 3/2011 | Sano | A61B 8/4455 600/443 |
| 2011/0306865 A1 | 12/2011 | Thornton | |
| 2012/0285250 A1* | 11/2012 | Rhim | A61N 7/02 73/632 |
| 2013/0217995 A1 | 8/2013 | Kruger | |
| 2013/0308425 A1* | 11/2013 | Nakamura | H01L 41/0825 367/87 |
| 2013/0312526 A1* | 11/2013 | Oishi | A61B 5/0095 73/620 |
| 2015/0016222 A1* | 1/2015 | Kandori | H05K 1/025 367/87 |
| 2015/0119684 A1* | 4/2015 | Furukawa | A61B 5/004 600/407 |
| 2015/0216504 A1* | 8/2015 | Kiyose | B06B 1/0629 600/472 |
| 2015/0268091 A1* | 9/2015 | Abe | G01H 11/06 367/181 |
| 2015/0290679 A1* | 10/2015 | Kandori | G10K 11/004 367/7 |
| 2015/0323657 A1* | 11/2015 | Machida | A61B 8/4444 600/459 |
| 2015/0365017 A1* | 12/2015 | Kandori | G01L 1/142 367/7 |
| 2016/0213257 A1* | 7/2016 | Nishihara | A61B 5/0095 |
| 2017/0059530 A1* | 3/2017 | Kandori | A61B 8/44 |

FOREIGN PATENT DOCUMENTS

| | | |
|---|---|---|
| JP | 2012033806 A | 2/2012 |
| JP | 2012179348 A | 9/2012 |
| JP | 2013229829 A | 11/2013 |

\* cited by examiner

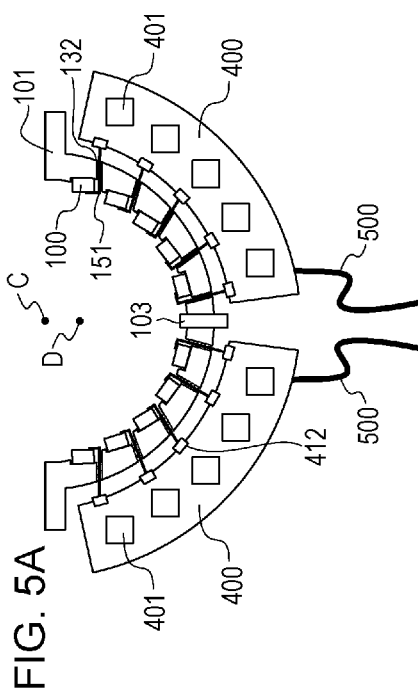
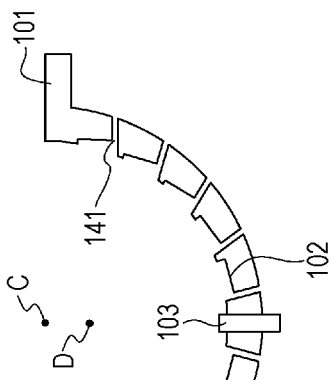
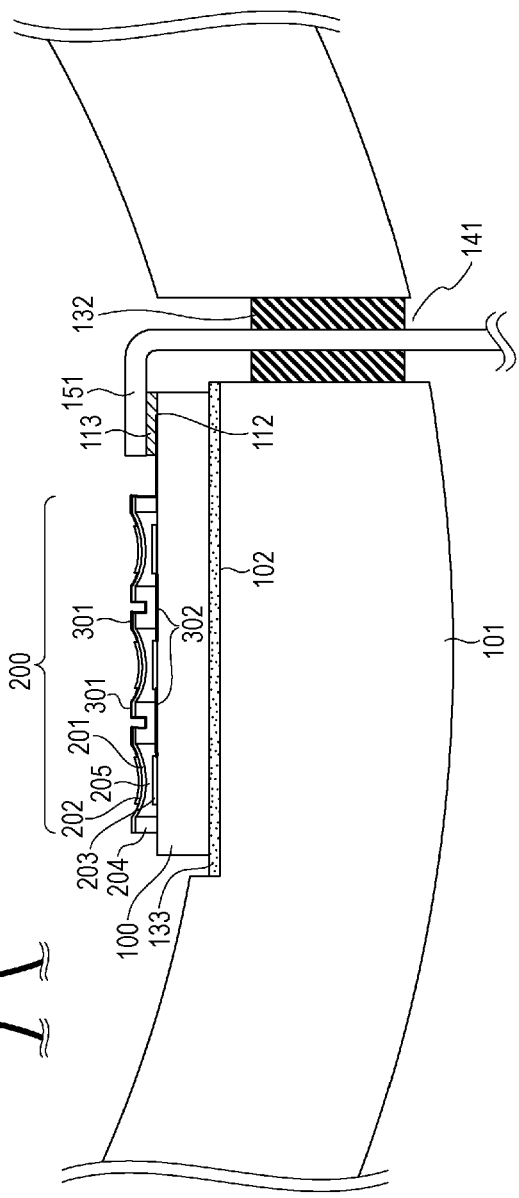

FIG. 7
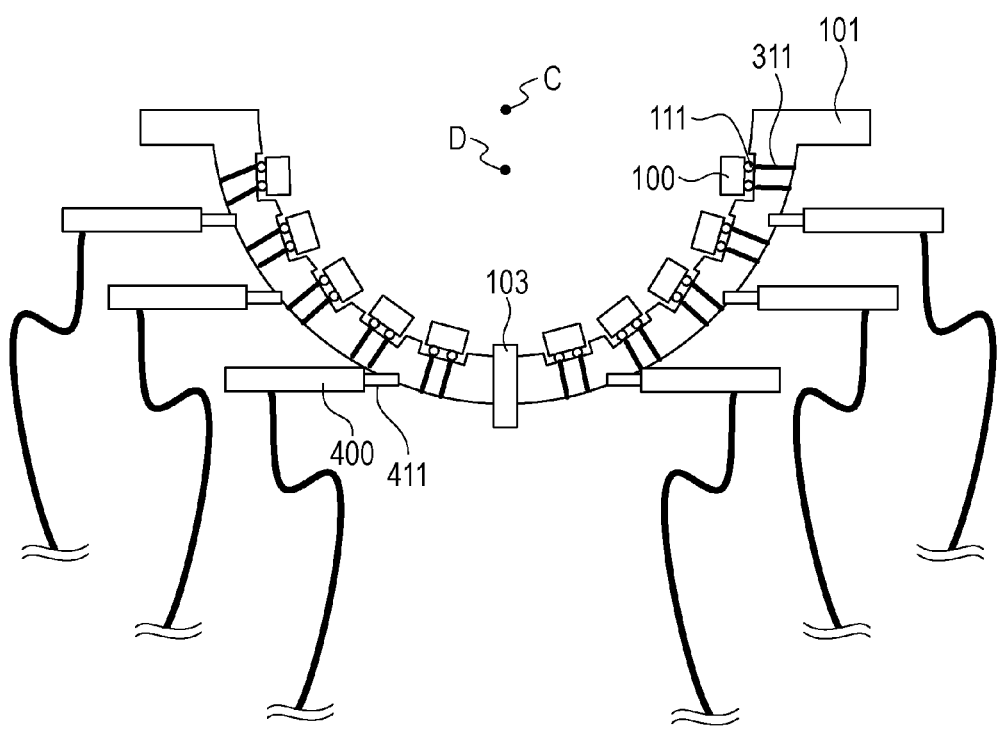
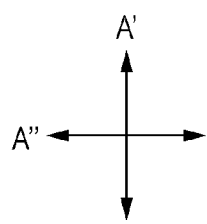

ULTRASOUND PROBE AND INFORMATION ACQUISITION DEVICE INCLUDING ULTRASOUND PROBE

TECHNICAL FIELD

The present disclosure relates to an ultrasound probe and an information acquisition device including the ultrasound probe.

BACKGROUND ART

A measuring system is available for applying light to a test object so that photoacoustic waves (ultrasound waves) are generated from a measurement object in the test object due to photoacoustic effects and receiving the generated ultrasound waves by using an ultrasound probe with a hemispherical surface shape. The ultrasound probe with the hemispherical surface shape includes a plurality of ultrasound transducer elements which are arranged on an inner wall surface of the hemisphere.

Explanation will be provided with reference to FIG. 16. In FIG. 16, 10 denotes a test object, 11 denotes a light source, 12 denotes an ultrasound probe, 13 denotes ultrasound transducers, 21 denotes a light beam, 22 denotes photoacoustic waves (ultrasound waves), and 30 denotes an acoustic matching material. The ultrasound probe 12 has a hemispherical surface shape, and includes the plurality of ultrasound transducers 13 and the light source 11. The test object 10 is arranged in such a manner that part of the test object 10 is surrounded by the ultrasound probe 12 with the hemispherical surface shape. The acoustic matching material 30 is filled between the test object 10 and the ultrasound probe 12. Light 21 is applied from the light source 11 to the test object 10, and the photoacoustic waves (ultrasound waves) 22 generated at the test object are received at the plurality of ultrasound transducers 13 included in the ultrasound probe 12. Thus, an image of the test object is obtained.

PTL 1 discloses the above-mentioned ultrasound probe with the hemispherical surface shape. Such an ultrasound probe with the hemispherical surface shape may include a larger number of ultrasound transducers whose reception surface may be directed toward a certain measurement point than an ultrasound probe on a plane. Therefore, measurement of the test object may be achieved with a higher sensitivity.

CITATION LIST

Patent Literature

PTL 1: US Patent Laid-Open No. 2011-0306865

In contrast, photoacoustic waves (ultrasound waves) generated from the test object contain different frequency components. The frequency components depend on the shapes, physical properties, and the like of sources of photoacoustic waves in the test object. Therefore, in order to faithfully reproduce the inside of the test object, it is necessary to receive photoacoustic waves (ultrasound waves) from the test object over a wide frequency band.

An electrostatic capacitance type transducer (Capacitive Micro-machined Ultrasonic Transducers, CMUT) is able to detect ultrasound waves over a wide frequency band. However, in order to increase the sensitivity of an ultrasound probe, it is necessary to provide as many ultrasound transducers as possible. Moreover, it is necessary for individual ultrasound transducers to have a planer chip shape or the like. However, an optimal configuration to provide such a chip on a surface with a hemispherical surface shape has not been known.

SUMMARY OF INVENTION

An ultrasound probe according to the present disclosure includes electrostatic capacitance type transducers with each transducer including a vibration film which includes a first electrode and a second electrode which is provided with a space between the vibration film and the second electrode, and a supporting member that has a curved surface on which the plurality of transducers are provided. An inner wall surface of the supporting member includes a plurality of flat surface parts, and the transducers are provided on the flat surface parts with plate-like substrates therebetween.

Further features of the present disclosure will become apparent from the following description of exemplary embodiments with reference to the attached drawings.

BRIEF DESCRIPTION OF DRAWINGS

FIGS. 5A, 5B, and 5C are cross-sectional views of an ultrasound probe according to an embodiment of the present disclosure.

FIG. 7 is a cross-sectional view of an ultrasound probe according to an embodiment of the present disclosure.

DESCRIPTION OF EMBODIMENTS

Hereinafter, embodiments of the present disclosure will be described with reference to the drawings. However, the present disclosure is not limited to the description provided below.

Ultrasound probes according to the embodiments include electrostatic capacitance type transducers (Capacitive Micro-machined Ultrasonic Transducers, CMUT) on an inner wall surface of a supporting member which has a curved surface. Since the CMUTs are provided, via plate-like substrates, on flat surface parts of the inner wall surface of the curved surface of the supporting member, the number of CMUTs whose reception surface may be directed toward a certain measurement point may be increased. Therefore, measurement of a test object may be achieved with a high sensitivity. Furthermore, with the use of the CMUTs, ultrasound waves over a wide frequency range may be received.

Hereinafter, specific configurations of ultrasound probes according to the embodiments of the present disclosure will be described in detail.

First Exemplary Embodiment (Ultrasound Probe)

Figure 1A:
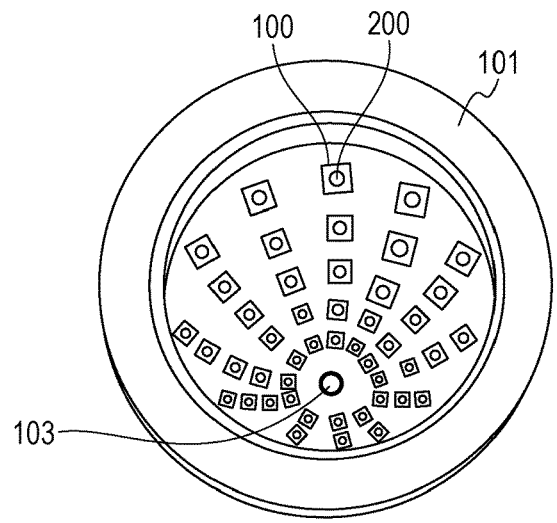
FIGS. 1A, 1B, 1C, and 1D are schematic diagrams explaining an ultrasound probe according to an embodiment of the present disclosure (FIG. 1A is an external view and FIG. 1B is a cross-sectional view).
Figure 1B:
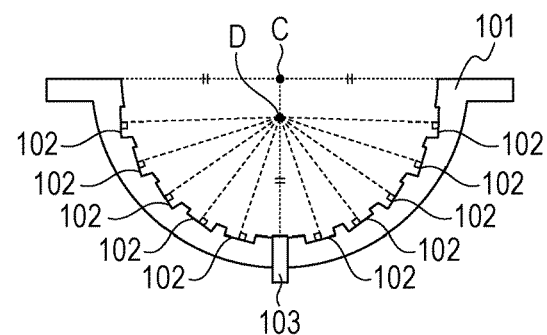

FIGS. 1A, 1B, 1C, and 1D are schematic diagrams for explaining an ultrasound probe according to this embodiment. FIG. 1A is an external view of the ultrasound probe, and FIG. 1B is a cross-sectional view of the ultrasound probe. In FIGS. 1A to 1D, 100 denotes plate-like substrates (chips), 101 denotes a supporting member having a curved surface, 102 denotes flat surface parts of the supporting member 101, 103 denotes a light source, and 200 denotes CMUTs.

The shape of the supporting member 101 is not particularly limited as long as it has a curved surface.

For example, it may be a hemispherical surface shape (dome-like shape), a truncated cone shape, a truncated pyramid shape, or a semi-cylindrical shape. Furthermore, the angle x formed by a line connecting the center and top of the sphere for the hemisphere and a line connecting the center of the sphere and an edge of the hemisphere is not limited to 90° (FIG. 1B). The angle may be smaller than 90° or greater than 90°.

A spherical surface is not limited to a sphere herein. The spherical surface may be rough to an extent which may be regarded as a spherical surface or may be an ellipsoid.

In this embodiment and the other embodiments, a case where the supporting member has a hemispherical surface shape will be explained.

In the ultrasound probe according to this embodiment, as illustrated in FIG. 1A, the plurality of plate-like substrates 100 on which the ultrasound transducers 200 are provided are provided on flat surface parts of the inner wall surface of the supporting member 101 which has a hemispherical surface shape. Furthermore, the light source 103 for applying light to a test object in the supporting member is provided in an appropriate manner. The position of the light source 103 is not limited to the position in FIGS. 1A to 1D.

The diameter of the hemisphere of the supporting member 101 may be set to, for example, equal to or greater than 1 cm and smaller than or equal to 100 cm. Furthermore, the size of the plate-like substrates 100 may be set to equal to or greater than 1 mm square and smaller than or equal to 10 cm square.

The inner wall surface of the hemisphere of the supporting member 101 includes, as illustrated in FIG. 1B, the recessed flat surface parts 102 in association with the number of the chips 100, and perpendicular lines of the flat surface parts 102 are arranged to be directed at a specific point D inside the hemispherical surface. The point D is set in association with the position where the test object is to be arranged inside the ultrasound probe with the hemispherical surface shape. It is important that the normal lines corresponding to reception surfaces of the plurality of transducers should cross each other at the single point, and the perpendicular lines corresponding to the plurality of flat surface parts do not necessarily cross each other at a single point on an inner side of the supporting member.

However, it is particularly preferable that the perpendicular lines corresponding to the plurality of flat surface parts of the supporting member cross each other at a single point on the inner side of the supporting member. In FIG. 1B, the point D is set in the vicinity of the center of curvature of the hemisphere. However, the point D is not limited to this.

Figure 1C:
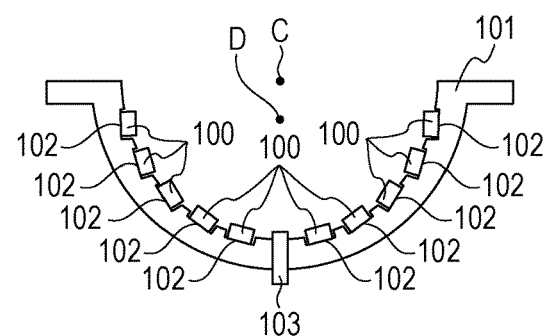
Figure 1D:
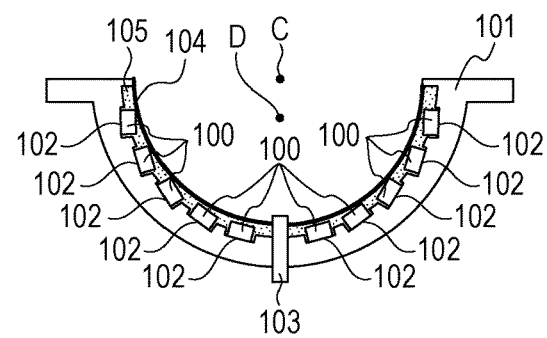

The chips 100 are arranged in a dispersed manner on the supporting member 101 with the hemispherical surface shape, as illustrated in FIG. 1C. In FIGS. 1C and 1D, 200 in FIGS. 1A and 1B are omitted.

With the uniform thickness of the chips 100, all the reception surfaces of the CMUTs 200 formed on the chips 100 on the flat surface parts 102 may be directed toward the point D. That is, the normal lines of the reception surfaces may be configured to be focused on the single point (D). Thus, the distance from the point D to each of the plurality of CMUTs 200 may be substantially the same. Consequently, in acquisition of an image of a test object using the ultrasound probe according to this embodiment, arithmetic processing for forming the image of the test object may be simplified.

Furthermore, since the flat surface parts 102 are recessed relative to the supporting member in association with the size of the chips 100, by filling the chips 100 in the recesses, the position of the chips may be determined easily. Therefore, the position of the CMUTs may be determined precisely with respect to the hemisphere of the supporting member 101, and the positional relationship for the individual CMUTs may be determined accurately. Consequently, the mutual positional relationship between the plurality of CMUTs 200 may be obtained accurately, and therefore later processing for forming an image may further be simplified.

The shape of the chips 100 may be, for example, a rectangular parallelepiped, a cylinder, or a polygonal column.

The CMUTs 200 used in this embodiment have characteristics of having an excellent responsiveness in reception of ultrasound waves and a wide frequency band, compared to piezo ultrasound transducers which are widely used today. However, since the CMUTs are to be formed on the chips, the CMUTs may be formed on a plane easily. However, it is difficult for the CMUTs to be arranged on a curved surface or the like. Therefore, in this embodiment, the chips 100 are separately formed for individual sound receiving elements, and the inner wall surface of the supporting member with the hemispherical surface shape includes the plurality of flat surface parts 102 associated with the shape of the chips 100. Moreover, with a configuration in which the chips 100 are arranged on the flat surface parts 102, the plurality of CMUTs 200 may be arranged on the curved surface, that is, the inner wall surface of the supporting member with the hemispherical surface shape.

That is, the ultrasound probe according to this embodiment, with the use of the CMUTs, has a characteristic of being able to receive ultrasound waves over a wide frequency range. In addition, since the plurality of CMUTs may be arranged on the inner wall surface of the hemispherical surface, an ultrasound probe with an excellent sensitivity may be provided.

For example, examples of the frequency range for reception of ultrasound waves include a range between 0.5 MHz and 6 MHz, inclusive, and a range between 1 MHz and 8 MHz, inclusive.

As a modification of this embodiment, as illustrated in FIG. 1D, a configuration is possible in which an insulating film 104 may be arranged over the chips 100 on which the CMUTs 200 are arranged, in such a manner that the CMUTs are covered with the insulating film 104. An adhesion layer 105 for adhesion between the insulating film 104; and the chips 100 and the CMUTs, is arranged therebetween. As the insulating film 104, a resin film, such as PET (Polyethylene Terephthalate) or PI (Polyimide), with a thickness which does not affect the transmission characteristics of photoacoustic waves may be used. In particular, it is desirable that, with the use of a PET film of 15 µm or less, less influence is exerted on the acoustic characteristics of ultrasound waves, and a higher insulation reliability is achieved. It is preferable that silicone rubber is used for the adhesion layer 105. This is because silicone rubber may achieve a high adhesiveness and excellent transmission characteristics of ultrasound waves and may obtain a characteristic of being less likely to affect the vibration characteristics of vibration films 201 of the CMUTs 200, which will be described later. It is more desirable that the thickness of the adhesion layer 105 is 10 µm or less, by which less influence is exerted on the transmission characteristics of ultrasound waves.

Furthermore, by providing the insulating film 104, the surface of the CMUTs 200 in which high voltage is applied to electrodes may be electrically insulated from the outside. Therefore, safety of the test object may be increased.

(CMUT)

Figure 2:
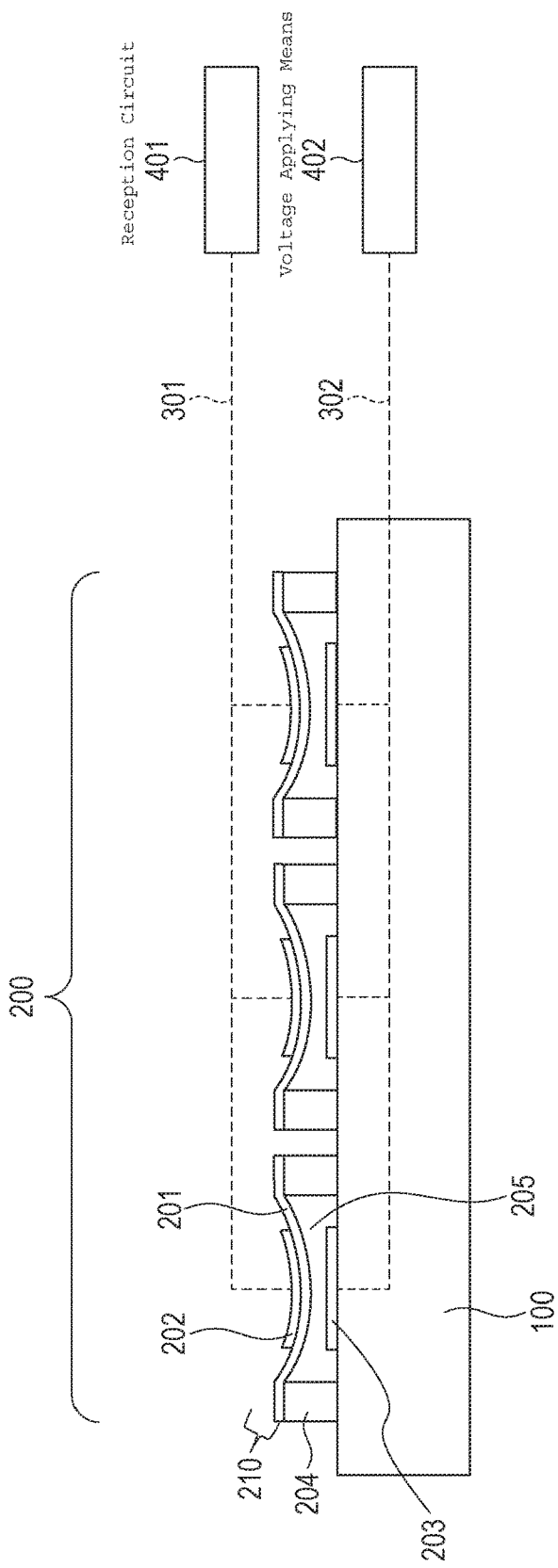
FIG. 2 is a cross-sectional view of a CMUT according to an embodiment of the present disclosure.

FIG. 2 is a schematic diagram explaining the CMUTs 200. In FIG. 2, 100 denotes the plate-like substrate (chip), 201 denotes a membrane, 202 denotes a first electrode, 203 denotes a second electrode, 204 denotes a supporting part, 205 denotes a space, 301 denotes first wiring, 302 denotes second wiring, 401 denotes a reception circuit, and 402 denotes voltage applying means for applying DC voltage. Hereinafter, the membrane 201 and the first electrode 202 may together be referred to as a vibration film 210. In FIG. 2, the CMUT in which three elements are provided on the plate-like substrate is illustrated. However, the number of elements may be smaller than 3 or greater than 3.

The membrane 201 is supported on the chip 100 by the supporting part 204 and is configured to vibrate in response to an ultrasound wave. The first electrode 202 is arranged on the membrane 201, and the vibration film 210 is arranged to face the second electrode 203 via the space. A pair of the first electrode 202 and the second electrode 203 which face each other with the membrane 201 and the space 205 therebetween is referred to as a cell.

The first electrode 202 is extracted out of the chip 100 via the first wiring 301, and is connected to the reception circuit 401. The second electrode 203 is extracted out of the chip 100 via the second wiring 302, and is connected to the voltage applying means 402. A potential difference, for example, between 1 V and 1000 V, inclusive, and from several 10 V to several 100 V, is generated between the first electrode 202 and the second electrode 203 by the voltage applying means 402. Due to vibration of the membrane 201 and the first electrode 202, the distance between the first electrode 202 and the second electrode 203 changes, and the electrostatic capacitance between the electrodes changes. Since there is a potential difference between the electrodes, minute current is generated in accordance with the change in the capacitance. The minute current is converted from current into voltage at the reception circuit 401, which is connected to the first electrode 202 and detects current, and is output. The intensity of an ultrasound wave may be measured based on the output voltage.

As illustrated in FIG. 2, the plurality of cells (201, 203, and 205) are arranged on the chip 100. Although numbers are assigned for a representative single cell, the same numbers are assigned for the other cells having the same shape.

The first electrodes 202 on the chip 100 are electrically connected to each other, and the second electrodes 203 on the chip 100 are electrically connected to each other. The first electrodes 202 on the chip 100 are connected to different reception circuits 401 for individual chips. In the ultrasound probe according to this embodiment, the number of reception circuits 401 is equal to the number of chips 100. The plurality of CMUTs 200 function as individual sound receiving elements (a unit of a sound receiving element is called an element) for the chips 100 on which the CMUTs 200 are arranged. The size of a sound receiving element may be set to, for example, equal to or greater than 100 µm and smaller than or equal to 10 mm. Although not particularly limited, 100 or more and 10000 or less sound receiving elements may be provided.

The configuration in which the first electrode 202 is arranged on the membrane 201 and the second electrode 203 is arranged on the substrate 100 has been explained above. However, this embodiment is not limited to this configuration. A configuration in which the first electrode 202 is connected to the reception circuit 401 and the second electrode 203 is connected to the voltage applying means 402 is also possible. Furthermore, the CMUTs according to this embodiment may be produced on silicon chips using a MEMS (Micro Electro Mechanical Systems) process adopting a semiconductor process.

Second Exemplary Embodiment

A second embodiment is different from the first embodiment in a method of connection between the CMUTs 200 on the chips 100 and the reception circuits 401. Hereinafter, only differences from the first embodiment will be explained, and explanation of common items may be found in previous paragraphs demoting the First Exemplary Embodiment.

Figure 3C:
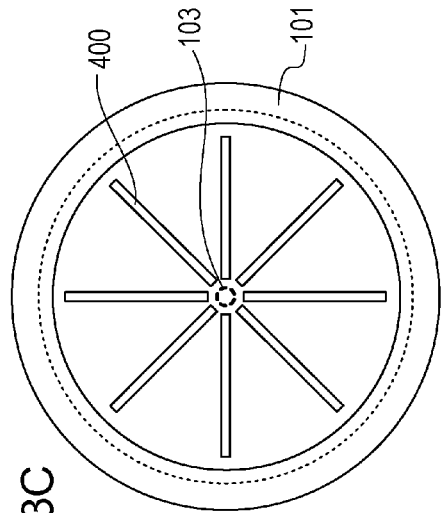
FIGS. 3A, 3B, and 3C are schematic diagrams explaining an ultrasound probe according to another embodiment of the present disclosure.
Figure 3A:
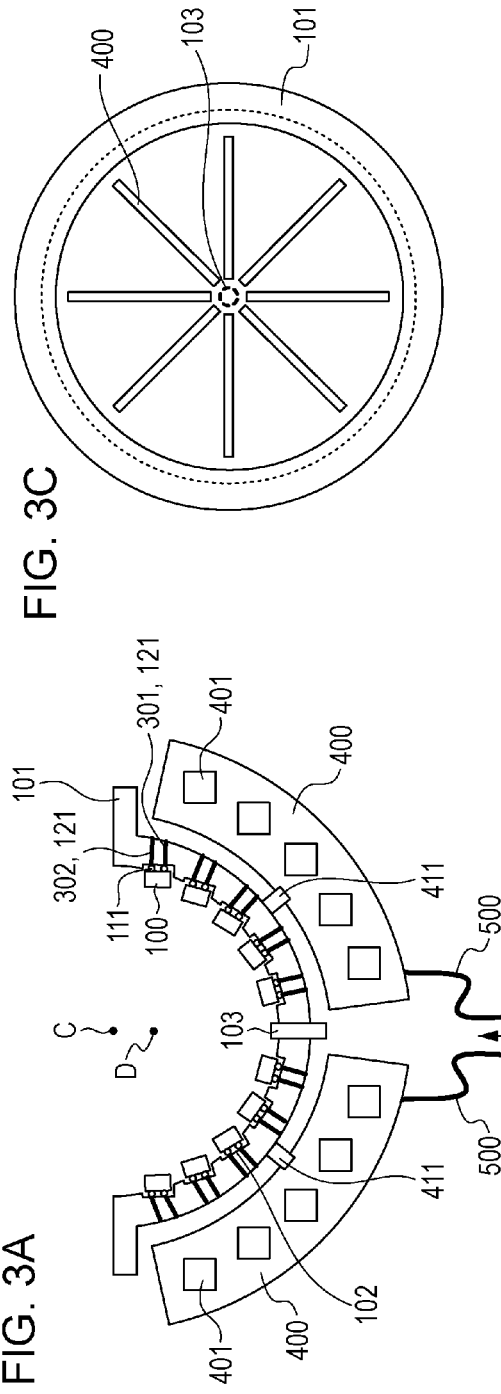

FIG. 3A is a schematic diagram of a cross-section of an ultrasound probe according to this embodiment. In this embodiment, wiring (through wiring 121) which penetrates through the supporting member 101 is provided, so that electrical connection from the flat surface parts 102 side (inner wall surface side) to an outer wall surface side of the supporting member 101 may be achieved. The two pieces of through wiring 121 are provided for each chip 100. On the outer wall surface of the supporting member 101, a connector 411 is arranged and wiring (not illustrated in the figure) connecting the through wiring 121 with the connector 411 is arranged. A circuit board 400 is connected to the connector 411. On the circuit board 400, the plurality of reception circuits 401 are arranged, and are connected to the CMUTs 200 (not illustrated in the figure) provided on the individual chips 100 via the connector 411 and the through wiring 121. For wiring for connection between the chips 100 and the reception circuits 401, components other than the connectors 411 and the through wiring 121 are not illustrated in the figure. Output from the reception circuits 401 are output to the outside via a cable 500 (wiring from the reception circuits 401 to the cable 500 is not illustrated in the figure).

With a configuration in which the plurality of reception circuits 401 are arranged on the circuit board 400, the circuit board 400 is connected to the connector 411, and the connector 411 is connected to the plurality of CMUTs, it is not necessary to provide the same number of connectors 411 as the number of CMUTs. Therefore, the number of components and the installation area may be reduced. Thus, even with a configuration including a large number of CMUTs, production is easily realized.

Furthermore, wires connected to the voltage applying means 402 and output signals from the reception circuits 401 provided at a single circuit board 400 are bundled as a single cable and connected to the outside. Thus, the number of cables in the entire ultrasound probe may be reduced, and compact wiring inside the ultrasound probe may be achieved.

The details of a configuration of connection between the chip 100 and the through wiring 121 will be explained with reference to FIG. 3B, which is an enlarged diagram of a peripheral part of a CMUT in FIG. 3A. Wiring 301 and 302 connected to the first electrode 202 and the second electrode 203 on the surface of the chip 100 are extracted to the rear face of the chip via wiring (through wiring 311) which penetrates through the chip 100. The rear face of the chip 100 and the flat surface part 102 of the supporting member 101 are connected through a bump 111. The bumps 111 are easily provided using solder bumps, gold bumps, or the like. With the use of the bumps 111, connection with excellent electrical connection may be achieved.

The wiring 301 and 302 are further extracted to the surface on the outer wall surface side of the hemisphere of the supporting member 101 via the through wiring 121 of the supporting member 101. Since the chip 100 includes the through wiring 311 and the rear face is connected through the bump, the size of a wiring extraction part may be reduced, and the size of the chip may be brought closer to the element size of the CMUT 200. Therefore, the CMUTs 200 may be arranged in more proximity, and the number of elements may be increased. Alternatively, with the same number of elements, a hemisphere with a smaller diameter may be achieved.

Furthermore, a configuration in which an underfill material is filled between the flat surface part 102 of the supporting member 101 and the chip 100 may be provided. Thus, the reliability of electrical connection of the bump 111 part may be improved.

FIG. 3C is a schematic diagram obtained when the ultrasound probe is viewed from a measurement object side (direction A in FIG. 3A). The circuit boards 400 are arranged in a parabolic manner from the center of the hemisphere.

In this embodiment, the circuit board 400 including the reception circuits 401 connected to individual elements is divided into plural substrates (divided into eight in FIG. 3C) and arranged. Thus, compared to the case where the circuit board 400 is not divided, the wiring length from the CMUT 200 to the reception circuit 401 may be shortened. Since the CMUTs 200 detect changes in electrostatic capacitance and perform operation for receiving ultrasound waves, longer wiring length deteriorates the reception characteristics.

Therefore, with the ultrasound probe according to this embodiment, deterioration in the reception characteristics caused by the influence of parasitic capacitance of wiring from the CMUTs 200 to the reception circuits 401 is small.

In reception of ultrasound waves, in order that a gas layer is not interposed between the ultrasound probe and the test object and acoustic mismatch does not occur, a liquid medium (acoustic matching material) is arranged and used. Since the ultrasound probe according to this embodiment uses the through wiring 121 for electrical connection inside the supporting member 101, the ultrasound probe has a configuration in which signal exchange may be performed via wiring but liquid from the inner wall surface side of the supporting member 101 does not enter the outer wall surface side. With this configuration, liquid may not enter the circuit board 400 side, and the characteristics of circuits and wiring may not be deteriorated. Thus, an ultrasound probe with high reliability may be provided.

Figure 4A:
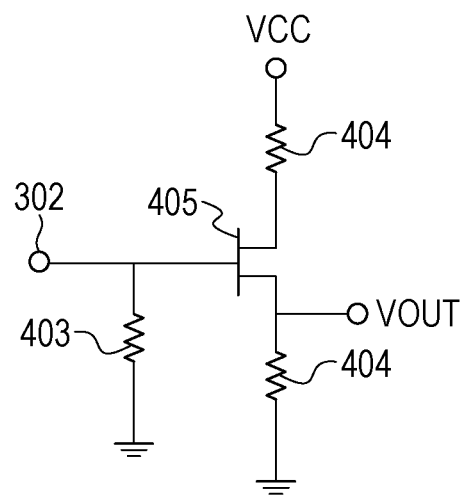
FIGS. 4A and 4B are diagrams explaining a reception circuit of the ultrasound probe according to an embodiment of the present disclosure.
Figure 4B:
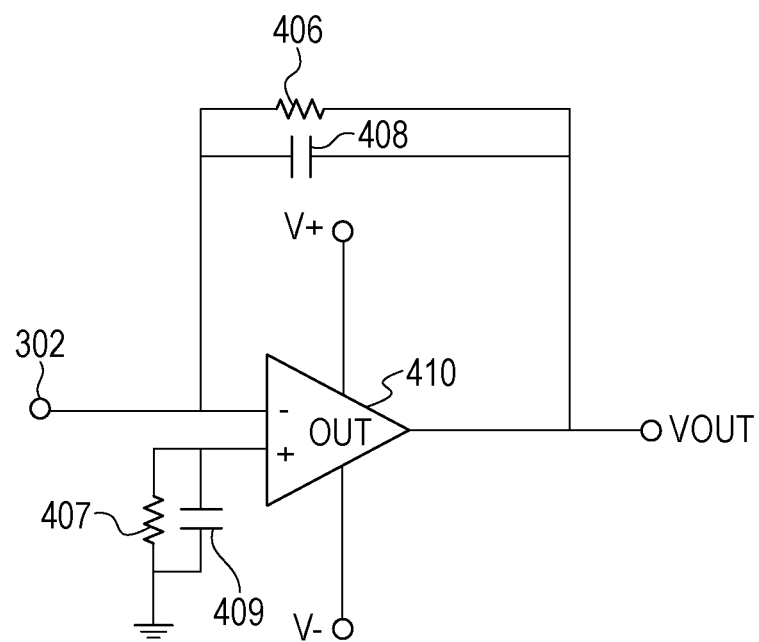

Next, the circuit details of the reception circuits 401 will be described with reference to FIGS. 4A and 4B. FIG. 4A illustrates a trans-impedance circuit using resistors and an FET, and FIG. 4B illustrates a trans-impedance circuit using an operational amplifier. In FIG. 4A, 403 and 404 denote resistors, and 405 denotes an FET. In FIG. 4B, 406 and 407 denote resistors, 408 and 409 denote capacitors, 410 denotes an operational amplifier, VCC, V+, and V− denote power supply terminals, and VOUT denotes an output terminal.

In FIG. 4A, a function is provided for converting voltage into current at the resistor 403 which is arranged for GND (reference potential), performing voltage amplification and impedance conversion at the FET 405, and outputting voltage. Since voltage-current conversion may be performed with such a simple circuit configuration, compact reception circuits 401 may be realized, the size of the circuit boards 400 may be reduced, and the size of the ultrasound probe itself may be reduced.

In contrast, in FIG. 4B, the resistor 406 and the capacitor 408 are arranged in parallel in a negative feedback part of the operational amplifier 410, and current input in a feedback part is converted into voltage. Due to the feedback property of an operational amplifier, with the use of a wide-band operational amplifier, the influence of parasitic capacitance at input wiring on current-voltage conversion efficiency may be reduced. Thus, compared to the case where the reception circuit 401 is arranged in proximity to the element 200 (case where the parasitic capacitance of wiring is extremely small), deterioration in current-voltage conversion is small, and excellent reception characteristics of ultrasound waves may be achieved.

As another form of this embodiment, an edge connector socket may be used for the connector 411. The circuit board 400 is a substrate (card edge connector) having a shape which achieves electrical connection by inserting the substrate directly into the connector. Since the circuit board 400 may be fixed by being inserted directly into the connector 411, the positional relationship between the supporting member 101 and the circuit board 400 may be fixed. Thus, the internal configuration of the ultrasound probe may be simplified.

Third Exemplary Embodiment

A third embodiment is different from the first and second embodiments in a method of connection between the CMUTs 200 on the chips 100 and the reception circuits 401. Hereinafter, only differences from the first and second embodiments will be explained, and explanation of common items may be found in previous paragraphs.

Specific explanation will be provided with reference to FIGS. 5A, 5B, and 5C, which are cross-sectional views of an ultrasound probe according to this embodiment. FIG. 5B is a diagram illustrating only the supporting member 101, the flat surface parts 102, the light source 103, and through holes 141 of FIG. 5A, and FIG. 5C is an enlarged diagram of FIG. 5A.

In FIGS. 5A and 5B, 132 denotes sealing materials, 133 denotes an adhesive, 141 denotes through holes, 151 denotes flexible print boards (flexible), and 412 denotes flexible print board connectors.

In this embodiment, the CMUTs 200 on the chips 100 and the reception circuits 401 are connected via the flexible print boards 151. As illustrated in FIG. 5B, the supporting member 101 has through holes 141 for individual flat surface parts 102. As illustrated in FIG. 5C, the chips 100 are adhered to the flat surface parts 102 of the supporting member 101 by the adhesive 133. Wiring 112 connected to the first electrodes 202 forming the CMUTs is electrically connected to the flexible print boards 151. A connection part 113 of the wiring 112 and the flexible print board 151 may be easily provided by using an anisotropic conductive resin, conductive paste, or the like.

In particular, the use of an anisotropic conducive resin is desirable since it brings about a function of electrical connection and physical adhesion between the chips 100 and the flexible print boards 151, and a simplified configuration and size reduction may be achieved. The flexible print boards 151 connected to the wiring 202 and 203 on the chips 100 pass through the through holes 141 of the supporting member 101 and are extracted to the outer wall surface side of the hemisphere face of the supporting member 101. The sealing materials 132 are filled in the through holes 141, so that liquid from the inner wall surface side of the hemisphere of the supporting member 101 does not enter the outer wall surface side.

In this embodiment, an anisotropic conductive resin is an insulating thermosetting resin containing fine conductive metallic particles of about several micrometers (equal to and more than 1 μm and less than or equal to 10 μm), and is, for example, an anisotropic conductive film (ACF), anisotropic conductive paste (ACP), or the like.

Furthermore, in this embodiment, conductive paste is obtained by mixing conductive powder into resin or the like, and is, for example, in a form in which silver, solder particles, or the like is dispersed in a thermosetting resin.

In this embodiment, the circuit board 400 includes the same number of flexible print board connectors 412 as the reception circuits 401 provided at the circuit board 400. The flexible print board 151 which passes through the through hole 141 and is extracted to the outer wall surface side of the hemisphere of the supporting member 101 is connected to the flexible print board connector 412 and is connected to the reception circuit 401 on the circuit board 400.

Figure 3B:
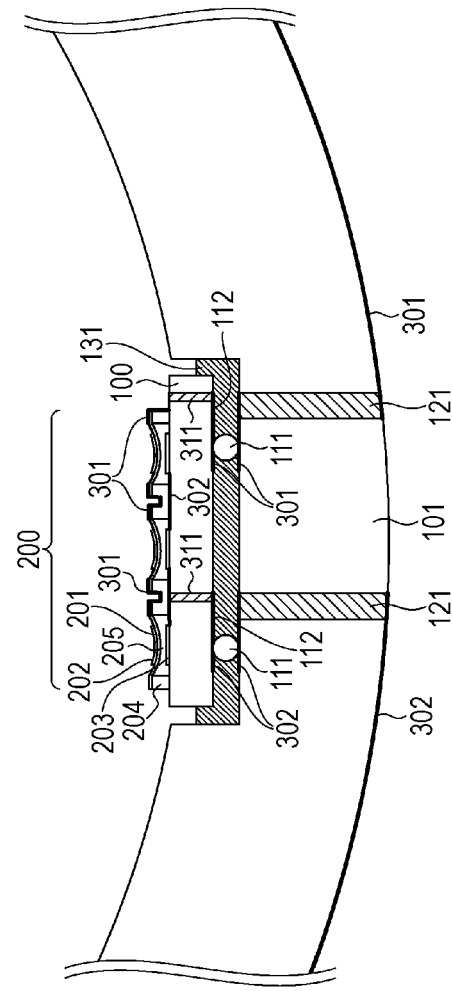

In this embodiment, compared to the connection method of FIGS. 3A to 3C according to the second embodiment, the element 200 and the reception circuit 401 may be connected in a more linear manner with a shorter distance. Therefore, the parasitic capacitance on wiring may be reduced. Thus, an ultrasound transducer with further excellent reception characteristics may be achieved.

Fourth Exemplary Embodiment

A fourth embodiment is different from the third embodiment in a method of connection between the CMUTs 200 on the chips 100 and the reception circuits 401. Differences from the third embodiment will be described.

Figure 6A:
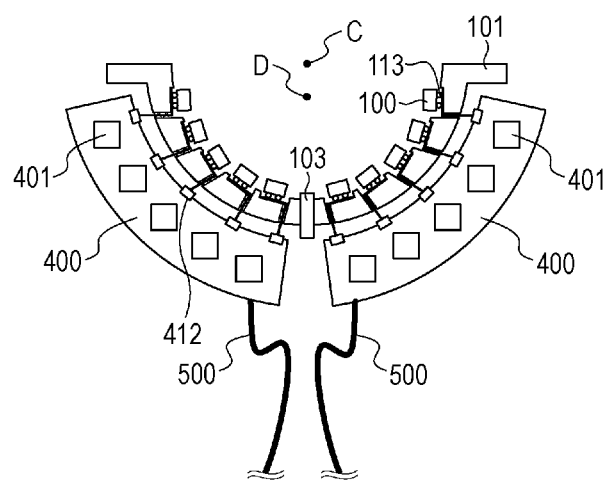
FIGS. 6A, 6B, and 6C are cross-sectional views of an ultrasound probe according to an embodiment of the present disclosure.
Figure 6B:
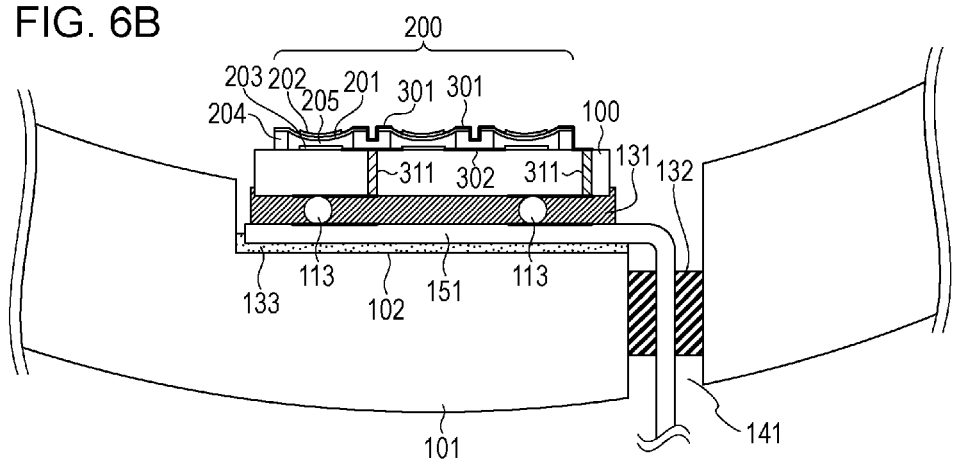

FIG. 6A is a cross-sectional view of an ultrasound probe according to this embodiment. In this embodiment, the chip 100 includes through wiring 311, and the chip 100 and the flexible print board 151 are connected by an electrical connection part 113 on the rear face of the chip 100. The electrical connection part 113 may be easily realized by using a solder bump, a gold bump, conductive paste, or the like. A part between the rear face of the chip 100 and the flexible print board 151 is filled with the sealing material 132, which is an insulating resin. Furthermore, the flexible print board 151 which is integrated with the chip 100 is fixed by the adhesive 133 on the flat surface part 102 of the supporting member 101.

In this embodiment, unlike the third embodiment, there is no need to provide a region where the connection part 113 is arranged on the chip 100 for connection with the flexible print board 151. Thus, the size of the chip may be brought closer to the element size of the CMUT 200. Therefore, the CMUTs may be arranged in more proximity, and the number of elements may be increased. Alternatively, in the case where the same number of CMUTs are provided, a supporting member with a hemispherical surface shape with a smaller diameter may be used.

Figure 6C:
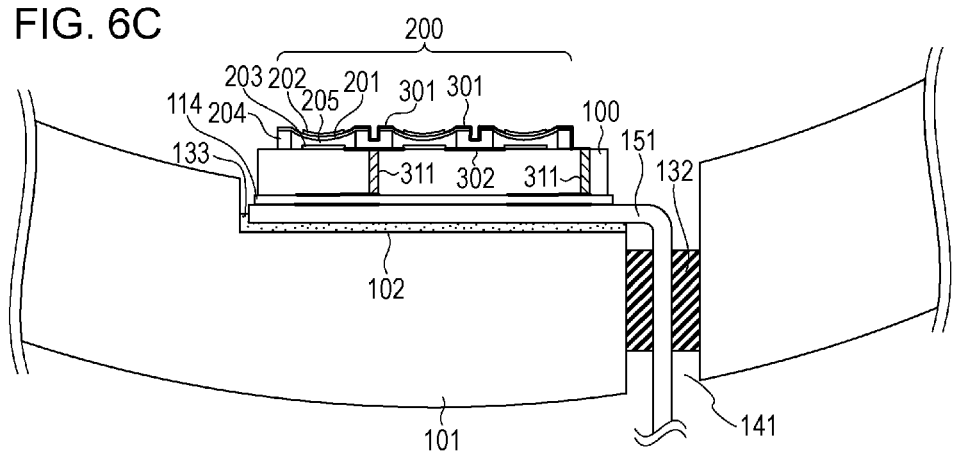

As a modification of this embodiment, a configuration in which an anisotropic conductive resin 114 is provided between the chip 100 and the flexible print board 151, as illustrated in FIG. 6C, may be provided. The anisotropic conductive resin (ACF) 114 is an insulating thermosetting resin containing fine conductive metallic particles. By applying pressure between electrodes to reduce the space between the electrodes to the diameter of conductive metallic particles or less and performing curing, electrical connection between the vertically arranged electrodes may be achieved. In contrast, since the distance between the electrodes arranged on the same plane is sufficiently wider than the fine conductive metallic particles, insulation is maintained in the state in which the fine conductive metallic particles are arranged in a dispersed manner in the insulating thermosetting resin. As described above, the anisotropic conductive resin 114 has two functions: electrical connection between the chip 100 and the flexible print board 151; and fixation between the chip 100 and the flexible print board 151. Therefore, electrical connection and adhesion may be achieved by one process, the implementation process may be simplified, and the number of component elements may be reduced. Thus, the yield may be improved. Furthermore, since electrical connection part on the rear face of the chip may be electrically insulated from the outside, the reliability may be increased.

Fifth Exemplary Embodiment

A fifth embodiment is different from the first and second embodiments in the arrangement of the circuit boards 400. Hereinafter, only differences from the first and second embodiments will be described. FIG. 7 is a cross-sectional view of an ultrasound probe according to this embodiment.

As illustrated in FIG. 7, the connectors 411 according to this embodiment are arranged in the direction (direction A" in FIG. 7) that is vertical to the depth direction (direction A' in FIG. 7) of the hemisphere. The direction of the circuit boards 400 are also arranged in the direction (direction A" in FIG. 7) that is vertical to the depth direction of the hemisphere. With this configuration, the depth direction of the hemisphere may be set to be substantially the same as the depth of the hemisphere. Therefore, constraints on the arrangement in the direction A' of the ultrasound probe according to this embodiment caused by the existence of the circuit boards 400 may be reduced.

Sixth Exemplary Embodiment

Figure 8:
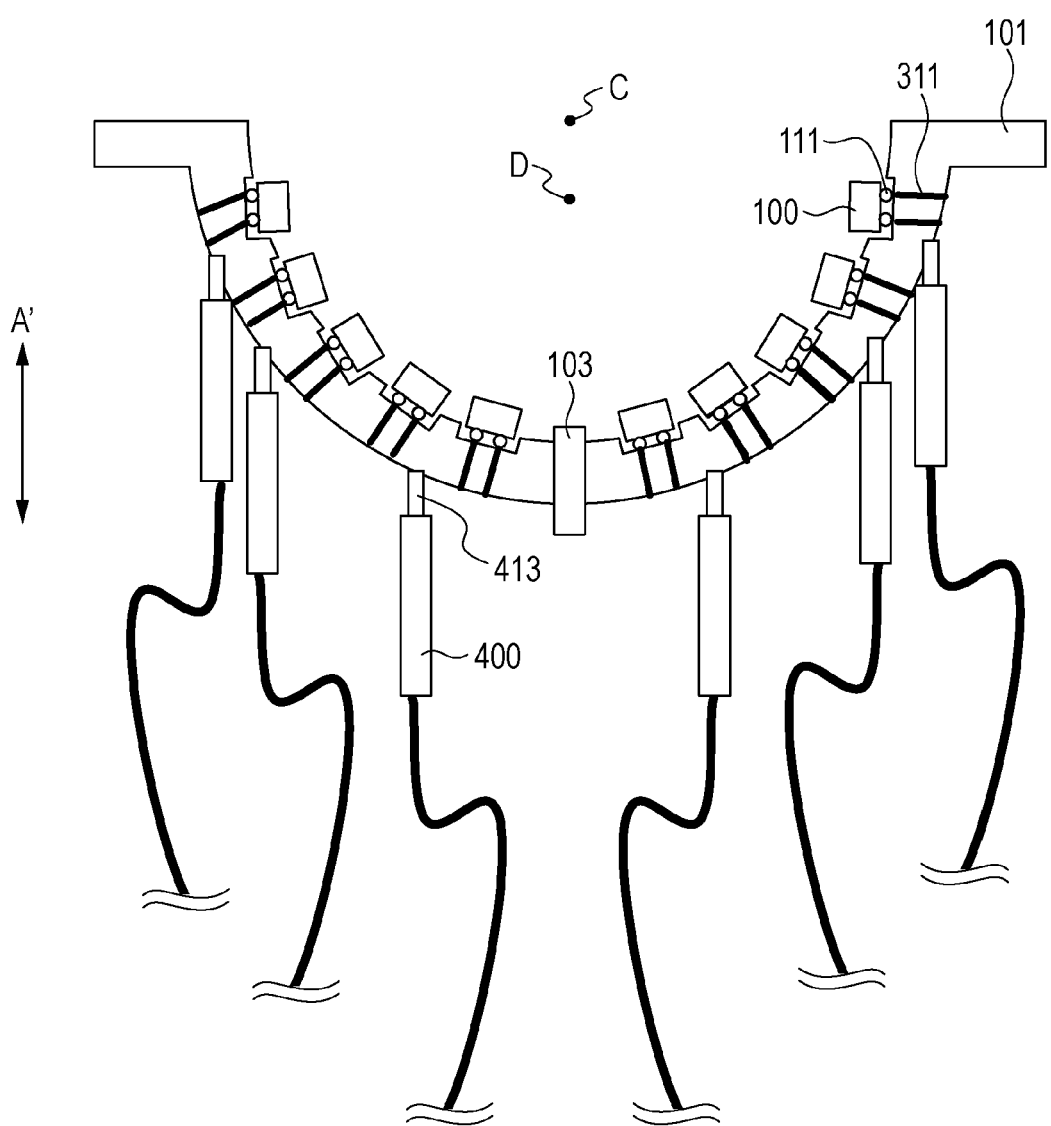
FIG. 8 is a cross-sectional view of an ultrasound probe according to an embodiment of the present disclosure.

A sixth embodiment is different from the fifth embodiment in the direction in which connectors 413 and the circuit boards 400 are arranged. Hereinafter, only differences from the fifth embodiment will be described. FIG. 8 is a cross-sectional view of an ultrasound probe according to this embodiment. The connectors 413 in this embodiment are characterized by being arranged toward the depth direction (direction A' in FIG. 8) of the hemisphere of the supporting member 101. The direction of the circuit boards 400 is also arranged along the depth direction (direction A' in FIG. 8) of the hemisphere.

In the ultrasound probe according to this embodiment, the circuit boards 400 are arranged toward the direction parallel to the depth direction of the hemisphere. Therefore, the circuit boards 400 may be accommodated within the range of the hemispherical surface shape when the outline circuit board of the ultrasound probe is viewed from the test object side. Thus, constraints on the arrangement in the direction A" of the ultrasound probe according to this embodiment caused by the existence of the circuit boards 400 may be reduced.

Seventh Exemplary Embodiment

A seventh embodiment is different from the first to sixth embodiments in that a probe with a hemispherical surface shape is configured by a combination of a plurality of divided probe units. Hereinafter, only differences from the first to sixth embodiments will be described. Common elements shared with the previous Exemplary Embodiments are incorporated by reference throughout.

Figure 9A:
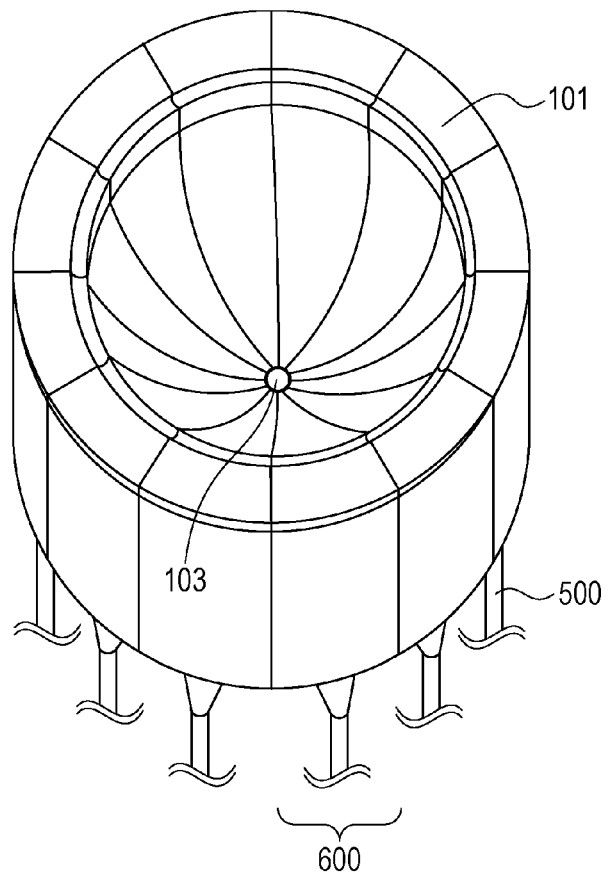
FIGS. 9A and 9B are schematic diagrams explaining an ultrasound probe according to an embodiment of the present disclosure.
Figure 9B:
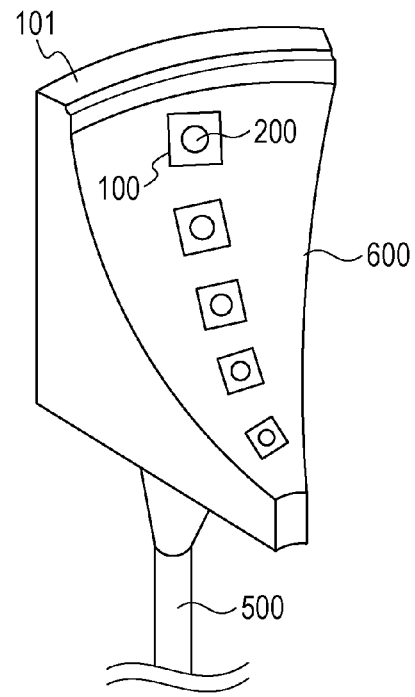

FIG. 9A is a schematic diagram of an ultrasound probe according to this embodiment. In FIG. 9A, a single ultrasound probe is configured by combining twelve ultrasound probe units. In FIG. 9A, although the CMUTs 200 and the substrates 100 are not illustrated, they are arranged in a manner similar to FIG. 1A. FIG. 9B illustrates ultrasound probe units 600. Each of the ultrasound probe units 600 includes the circuit board 400 (not illustrated in the figure) and the cable 500, and is arranged within a casing. By adhering or fixing the plurality of ultrasound probe units, an ultrasound probe may be easily configured.

Since the ultrasound probe according to this embodiment is configured by combining a plurality of probe units, the yield may be improved compared to the case where an ultrasound probe is produced in an integrated manner.

Eighth Exemplary Embodiment

An eighth embodiment is different from the first to seventh embodiments in the circuit configuration for applying DC voltage to the second electrodes 203. Hereinafter, only differences from the first to seventh embodiments will be described.

Figure 10A:
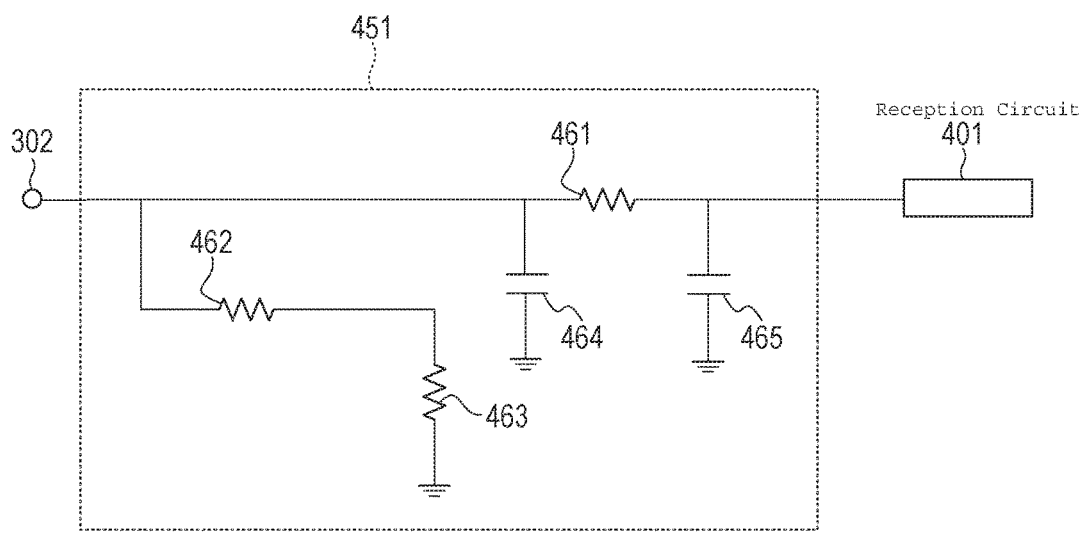
FIGS. 10A and 10B are schematic diagrams illustrating an adjustment circuit for applied voltage of an ultrasound probe according to an embodiment of the present disclosure.

In FIG. 10A, 451 denotes application voltage adjusting means. This embodiment is characterized by including the application voltage adjusting means 451 between the voltage applying means 401 for applying DC voltage and the second wiring 302. The application voltage adjusting means 451 has a function to adjust a potential Vb output from the voltage applying means 401 to Vo, which is different from Vb, at a terminal for application to the second electrode 203 connected to the second wiring 302.

In a CMUT, an optimal value of DC voltage to be applied for each cell or each element including a plurality of cells differs according to thickness variations of the membranes 201 or variations of the spaces 205. The ultrasound probe according to this embodiment has a function to apply optimal DC voltage Vo for each cell or each element of a CMUT. The circuit configuration of the application voltage adjusting means 451 will be explained with reference to FIG. 10A.

The application voltage adjusting means 451 includes three voltage-dividing resistors. A first voltage-dividing resistor 461 is inserted between the voltage applying means 401 and the second electrode 203. Furthermore, a second voltage-dividing resistor 462 and a third voltage-dividing resistor 463 are connected in series, and are arranged between the wiring 302 connected to the second electrode 203 and a GND terminal. Here, the resistance of the first voltage-dividing resistor 461 is denoted by R1, the resistance of the second voltage-dividing resistor 462 is denoted by R2, and the resistance of the third voltage-dividing resistor 463 is denoted by R3. At this time, the voltage value Vo applied to the wiring 302 on the second electrode 203 side may be expressed by $Vo=(R2+R3)/(R1+R2+R3)\times Vb$, and different optimal voltages may be applied to a CMUT for individual elements.

This embodiment is characterized by setting the value of R2 to be smaller than the value of R3. Therefore, a drop voltage at the second voltage-dividing resistor 462 is smaller than a voltage drop at the third voltage-dividing resistor 463. Thus, although it is necessary for the first voltage-dividing resistor 461 and the third voltage-dividing resistor 463 to have a high breakdown voltage (from several ten volts to several hundred volts), the second voltage-dividing resistor 462 may use a lower breakdown voltage. The first voltage-dividing resistor 461 and the third voltage-dividing resistor 463 have high breakdown voltage, and therefore, they are large components. However, a compact component may be used for the second voltage-dividing resistor 462.

Due to the existence of the second voltage-dividing resistor, even if the resistances of the first voltage-dividing resistor 461 and the third voltage-dividing resistor 463 are fixed, only by changing the resistance of the second voltage-dividing resistor 462, application voltage may be changed. The second voltage-dividing resistor 462 may be set to have a resistance which realizes an application voltage corresponding to each element. The second voltage-dividing resistor 462 is a compact component, and replacement of the second voltage-dividing resistor 462 may thus be easily performed.

Furthermore, a first high-voltage capacitor 464 and a second high-breakdown-voltage capacitor 465 are arranged in order to suppress variations in the voltage of each terminal and entry of noise from the outside.

The ultrasound probe according to this embodiment is able to apply an optimal DC voltage for each element. Therefore, uniform characteristics may be achieved among CMUTs, and data acquisition may be attained with high accuracy. Thus, with the use of the ultrasound probe according to this embodiment, a high-quality image may be obtained.

Figure 10B:
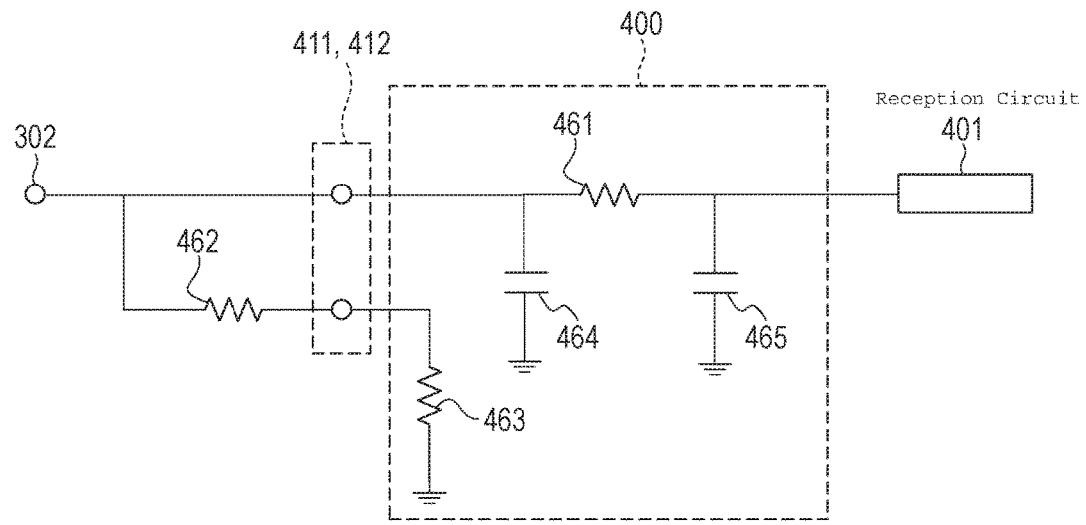

As another form of this embodiment, as illustrated in FIG. 10B, a configuration may be provided in which the second voltage-dividing resistor 462 is arranged closer to the second electrode 203 by the connector 411 (or 412). The first voltage-dividing resistor 461 and the third voltage-dividing resistor 463 are arranged on the circuit board 400. The second voltage-dividing resistor 462 is set to have a resistance which realizes an application voltage corresponding to each element, and different values are used for individual elements. Therefore, even if an element (element) to be inserted into a connector is replaced with a different one, an optimal application voltage may be set for each element, without changing the value of a resistor to be mounted on the circuit board 400. Furthermore, since the second voltage-dividing resistor 462 has a small breakdown voltage and is a compact component, the same number of second voltage-dividing resistors 462 as the elements may be arranged on the supporting member 101 (or the flexible print board 151).

Wiring connected to the circuit board 400 through a connector includes third wiring 303 connected to the second voltage-dividing resistor 462, in addition to the first wiring 301 connected to the first electrode 202 and the second wiring 303 connected to the second electrode 203. Thus, even if the second voltage-dividing resistor 462 is arranged closer to the first electrode 202 by a connector, the voltage Vo to be applied to the CMUT may be adjusted.

In an ultrasound probe according to the different from of this embodiment, even if a CMUT is replaced with a different CMUT, only by changing a connector, an optimal DC voltage may be applied for each element. Therefore, replacement may be performed easily, and an ultrasound probe with uniform CMUT characteristics may be provided.

Ninth Exemplary Embodiment

A ninth embodiment is different from the first to eighth embodiments in that not only the CMUTs 200 that receive ultrasound waves but also CMUTs 199 that transmit ultrasound waves are provided. Hereinafter, differences from the first to eighth embodiments will be described.

In the ultrasound probe according to this embodiment, the plurality of transducers are provided on the plate-like substrate. At least one of the plurality of transducers is able to receive an ultrasound wave, and at least one of the plurality of transducers is able to transmit an ultrasound wave.

Figure 11:
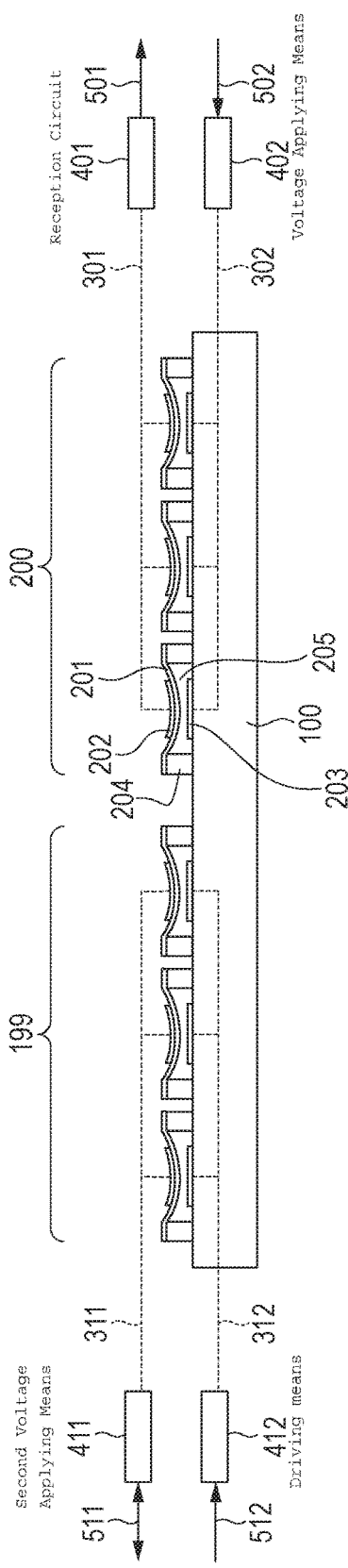
FIG. 11 is a cross-sectional view of an ultrasound probe according to an embodiment of the present disclosure.

In FIG. 11, 199 denotes a CMUT that transmits an ultrasound wave, 411 denotes second voltage applying means for applying DC voltage, and 412 denotes driving means. FIG. 11 is a schematic diagram of the CMUTs 199 and 200 which are arranged on a single chip 100. The individual elements of CMUT 199 and the CMUT 200 are arranged on each chip 100. The CMUT 199 has characteristics suitable for transmission of an ultrasound wave. The second voltage applying means 411 is set to an application voltage which achieves an optimal ultrasound wave transmission efficiency. Furthermore, the driving means 412 may apply a high-voltage pulse to the second electrode. The first electrode 202 of the CMUT 199 is electrically connected to the driving means 412 for each chip 100. Thus, electrostatic attraction generated between the first electrode 212 and the second electrode 203 is changed by the driving means 412, which causes the membrane 201 to vibrate, and an ultrasound wave is transmitted.

In contrast, the CMUT 200 has a configuration which is suitable for reception of an ultrasound wave, in addition to a photoacoustic wave. The membrane 201 is caused to vibrate in response to reception of a photoacoustic wave (ultrasound wave), and the vibration may be detected at the detection circuit 401.

In this embodiment, at the time of formation of an ultrasound imaging data image, an ultrasound wave is transmitted toward a test object from the CMUT 199, and an ultrasound wave reflected by the test object is received by the CMUT 200. In contrast, at the time of acquisition of an ultrasound imaging image, an ultrasound wave generated at the test object by the light source 103 is received at the CMUT 200.

With the use of the ultrasound probe according to this embodiment, reception of ultrasound waves and transmission and reception of ultrasound waves may be performed with a single probe. Therefore, a photoacoustic imaging image and an ultrasound imaging image may be formed based on detected data. Furthermore, the CMUT 199 which is suitable for transmission of an ultrasound wave and the CMUT 200 which is suitable for reception of a photoacoustic wave (ultrasound wave) are separately provided. Therefore, excellent ultrasound wave transmission characteristics and excellent reception characteristics may be achieved at the same time, and a high-quality image may thus be obtained. Furthermore, since the CMUTs 199 and 200 to be used for transmission and reception of ultrasound waves and for reception of ultrasound waves are formed on the same chip 100, an image with less positional shift of a photoacoustic imaging image and an ultrasound imaging image may be obtained.

Tenth Exemplary Embodiment

A tenth embodiment is different from the first to eighth embodiments in that CMUTs also have a function to perform transmission and reception of ultrasound waves. Hereinafter, differences from the first to eighth embodiments will be described.

Figure 12A:
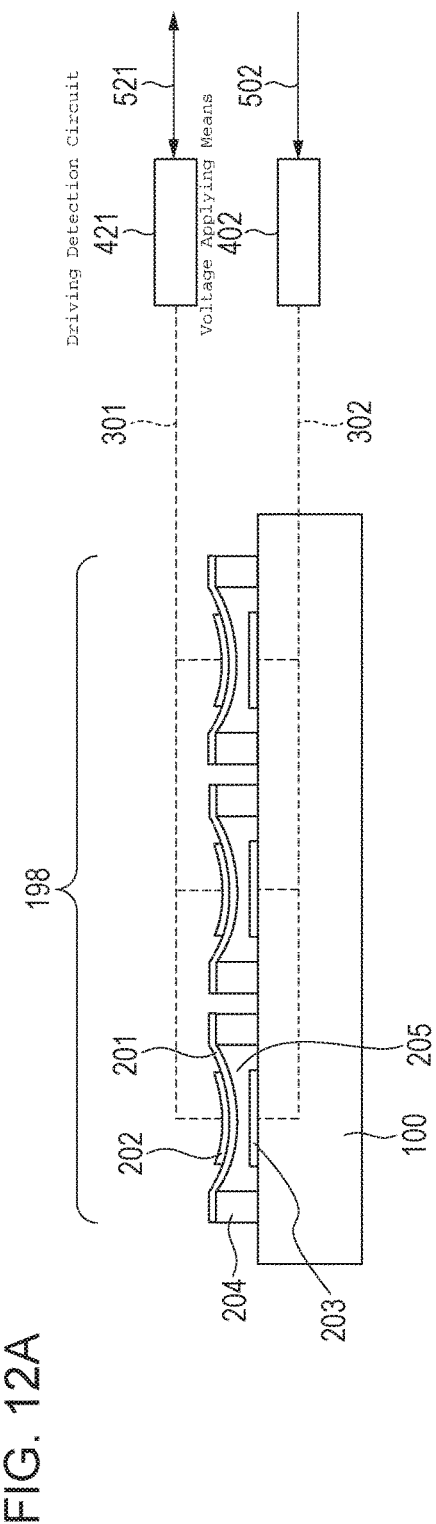
FIGS. 12A and 12B are schematic diagrams explaining an ultrasound probe according to an embodiment of the present disclosure.
Figure 12B:
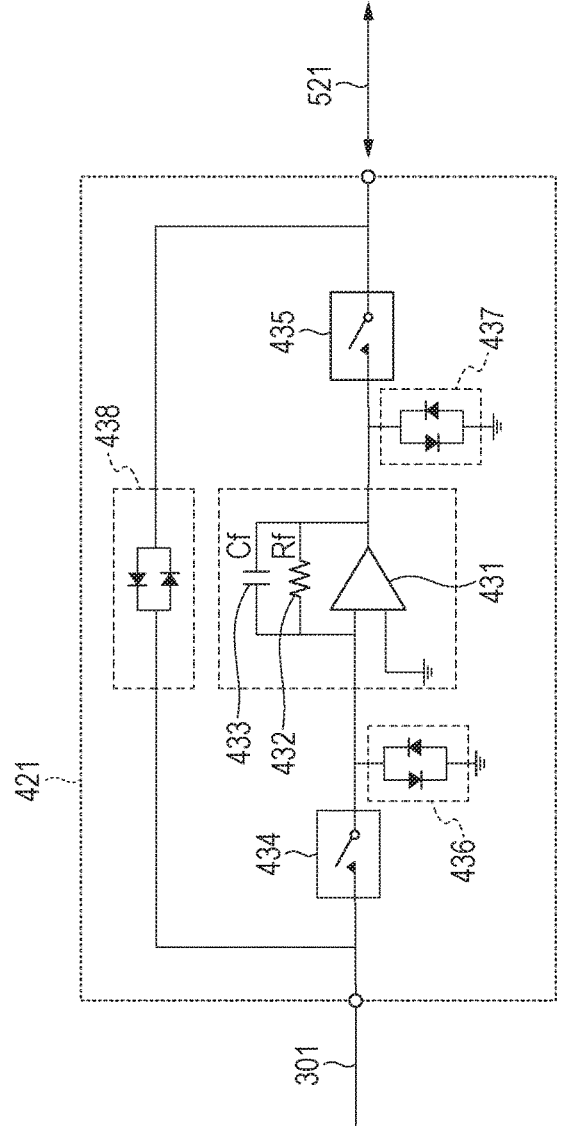

In FIGS. 12A and 12B, 421 denotes a driving detection circuit, 431 denotes an operational amplifier, 432 denotes a feedback resistor, 433 denotes a feedback capacitance, 434 and 435 denote high-breakdown-voltage switches, 436 and 437 denote diodes, and 438 denotes a high-breakdown-voltage diode. FIG. 12A is a schematic diagram of the CMUT 198 which is arranged on a single chip 100. On the single chip, one element (element) of the CMUT 198 is arranged, and the first electrode 202 of the CMUT 198 is connected to the driving detection circuit 421. The driving detection circuit 421 has a function to apply a high-voltage pulse to be used for transmission of an ultrasound wave from a device side to the CMUT 198 and output minute current from the CMUT 198 as a detection signal to the device side.

FIG. 12B is a circuit diagram for explaining the details of the driving detection circuit 421. The feedback resistor 432 and the feedback capacitance 433 are arranged in parallel in a negative-feedback part of the operational amplifier 431, and a function to perform current-voltage conversion is provided. The high-breakdown-voltage switches 434 and 435 and the diodes 436 and 437 are connected to input and output terminals of the operational amplifier. For the high-breakdown-voltage diode 438, in the case of a predetermined voltage (just below 1 volt) or less between terminals, wiring connection between the terminals is interrupted. Furthermore, for the high-breakdown-voltage switches 434 and 435, when a voltage higher than a predetermined voltage (about several volts) are applied, wiring between input and output terminals of the switches is disconnected.

When a high-voltage pulse for transmission is not applied, there is a negligible potential difference between the terminals of the high-breakdown-voltage diode 438, the high-breakdown-voltage diode 438 is in a state in which wiring at input and output terminals is disconnected. In contrast, since high voltage is not applied from the outside to the highbreakdown-voltage switches 434 and 435, wiring between the switches is connected. Therefore, minute current from a transducer may be subjected to current-voltage conversion at the operational amplifier, and a detection signal may be output to a device (not illustrated in the figure) connected to the outside.

In contrast, when a high-voltage pulse for transmission is applied from a device (not illustrated in the figure) side, wiring inside the high-breakdown-voltage diode 438 is connected, and a voltage higher than a predetermined voltage (about several volts) is applied to the high-breakdown-voltage switches 434 and 435. Therefore, the high-breakdown-voltage switches 434 and 435 disconnect the wiring inside the switches. Thus, the operational amplifier may be prevented from being damaged by being applied with high voltage. Since signal output from the operational amplifier is cut at the high-breakdown-voltage switch 435, the signal output will not affect high-voltage pulses applied for transmission. Therefore, a high-voltage pulse for transmission of an ultrasound wave may be applied to the first electrode of the transducer.

With the ultrasound probe according to this embodiment, reception of ultrasound waves and transmission and reception of ultrasound waves may be performed with a single probe. Therefore, a photoacoustic imaging image and an ultrasound imaging image may be formed based on detected data. Furthermore, with the use of the single CMUT 198 to be used for transmission of an ultrasound wave and reception of a photoacoustic wave or an ultrasound wave, the size of the chip 100 may be reduced. Thus, the CMUTs 198 may be arranged in more proximity, and the number of elements may be increased. Alternatively, with the same number of elements, a hemisphere with a smaller diameter may be achieved. Furthermore, since the CMUTs 198 are used for multiple purposes, an image with less positional shift of a photoacoustic imaging image and an ultrasound imaging image may be obtained.

Eleventh Exemplary Embodiment

An eleventh embodiment is different from the ninth embodiment in that the number of cells to be used for transmission ultrasound waves is different from the number of cells to be used for reception of ultrasound waves. Hereinafter, differences from the ninth embodiment will be described.

In FIGS. 13A, 13B, 13C, and 13D, 197 denotes a first CMUT, and 196 denotes a second CMUT.

Figure 13A:
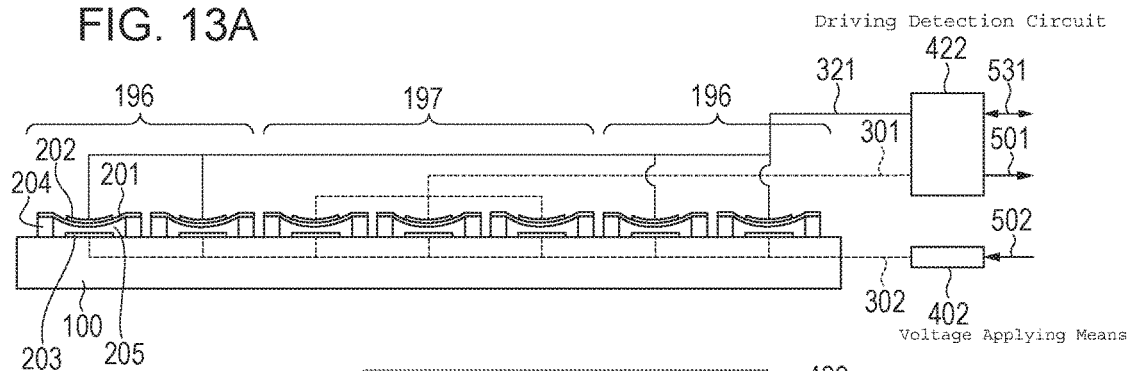
FIGS. 13A, 13B, 13C, and 13D are schematic diagrams explaining an ultrasound probe according to an embodiment of the present disclosure.

This embodiment is characterized in which the second CMUT 196 is used for reception of an ultrasound wave and only the first CMUT 197 is used for transmission and reception of an ultrasound wave. FIG. 13A is a cross-sectional view of the first CMUT 197 and the second CMUTs 196. The first CMUT 197 and the second CMUTs 196 are arranged on a single chip 100.

The first electrode 202 of the first CMUT 197 is connected to a first terminal 441 of a driving detection circuit 422. The second electrode 203 of the second CMUT 196 is connected to a second terminal 442 of the driving detection circuit 422. The driving detection circuit 422 has a configuration in which a current-voltage conversion circuit (trans-impedance circuit) using an operational amplifier and an addition device 439 are added to the circuit explained in the tenth embodiment. Hereinafter, only differences from the tenth embodiment will be explained.

Figure 13B:
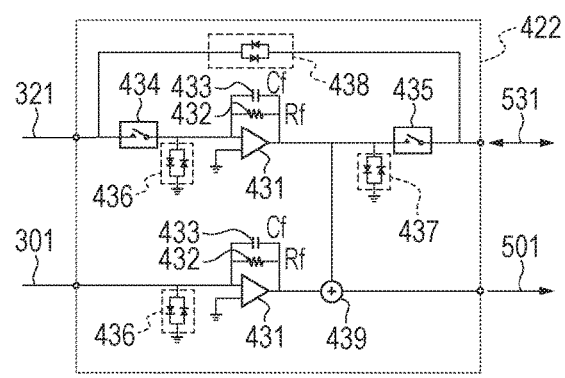

FIG. 13B is a circuit diagram explaining the driving detection circuit 422 of the ultrasound probe according to this embodiment. In reception of an ultrasound wave, the high-breakdown-voltage diode 438 is turned off, and wiring before and after the operational amplifier is turned on. Therefore, current from the first CMUT 197 is converted into voltage. A signal 501 obtained at an addition circuit 439 by adding a voltage signal of the first CMUT 197 and a reception signal from the second CMUT 196 obtained by converting current into voltage is used as a reception signal. Thus, ultrasound waves may be received at all of the first CMUT 197 and the second CMUT 196.

In contrast, in transmission and reception of an ultrasound wave, an ultrasound wave driving signal is input as 531 to the driving detection circuit 422. When high voltage is applied, the operational amplifier is protected by the high voltage, and the high-breakdown-voltage diode 438 is turned on. Therefore, driving voltage is applied only to the first CMUT 197 connected to wiring 321, and an ultrasound wave is transmitted through the vibration film. When the vibration film is caused to vibrate due to an ultrasound wave reflected by the test object (measurement object), the ultrasound wave transmission (driving) signal 531 is not applied. Therefore, since the high-breakdown-voltage diode 438 is turned off and the wiring before and after the operational amplifier is turned on, current-voltage conversion is performed, and the ultrasound wave reception signal 531 is output.

In the ultrasound probe according to this embodiment, the size of the CMUT to be used for reception of an ultrasound wave may be different from the size of the CMUT to be used for transmission and reception of an ultrasound wave. Therefore, since reception of ultrasound waves and transmission and reception of ultrasound waves may be performed with elements having sizes suitable for corresponding signal acquisition, data necessary for generating a high-quality photoacoustic imaging image and a high-quality ultrasound imaging image may be obtained.

Furthermore, in this embodiment, the size of the CMUTs (197 and 196) to be used for reception of ultrasound waves is greater than the size of the CMUT (197) to be used for transmission and reception of an ultrasound wave. Since the size of the CMUTs for reception of ultrasound waves is large, the directivity of ultrasound waves to be received may be increased when CMUTs are used at the same frequency. In contrast, in the case of transmission and reception of ultrasound waves, even if CMUTs with a small diameter are used, the directivity of the CMUT at the time of transmission is multiplied with the directivity of the CMUT at the time of reception. Therefore, compared to the CMUT with the same diameter which performs only reception, the directivity after transmission and reception may be increased. Thus, with the ultrasound probe according to this embodiment, an image in which the resolution of a photoacoustic imaging image is closer to the resolution of an ultrasound imaging image may be obtained.

Figure 13C:
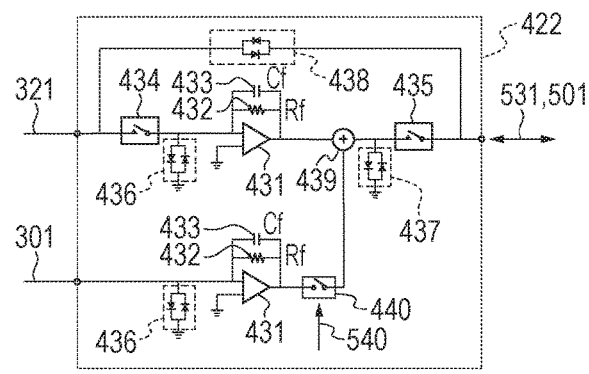

As another form of this embodiment, the driving detection circuit 422 illustrated in FIG. 13C may be used. The driving detection circuit 422 according to this embodiment is characterized by including a switch 440 between the operational amplifier 431 connected to the second CMUT 196 and the addition device 439. Turning on and off of the switch 440 is controlled by a switch control signal 540. Specifically, the control signal 540 is input so that the switch is turned off at the time of transmission and reception of an ultrasound wave and turned on at the time of reception of an ultrasound wave. The switch 440 may be easily realized by using a low-voltage analog switch.

In this embodiment, the ultrasound wave transmission reception signal 531 and the ultrasound wave output signal 501 may use a single piece of wiring, and the number of wiring in a cable of the probe may thus be reduced. The switch control signal 540 is not necessarily input from an external device. With provision of means for detecting that a high-voltage pulse as a driving signal is applied in the ultrasound probe and generating a switch OFF signal for a certain period of time, signal input from the outside may be prevented.

Figure 13D:
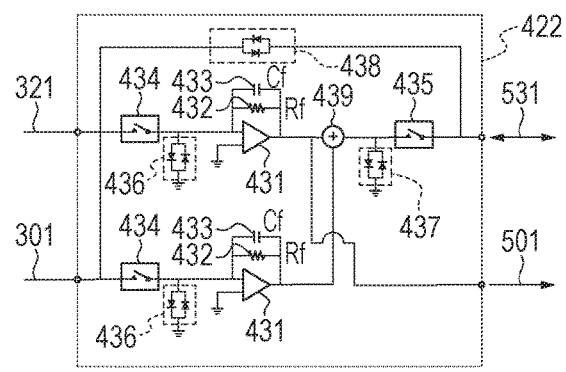

As another example of this embodiment, as illustrated in FIG. 13D, a configuration in which only the first CMUT 197 is used for reception of an ultrasound wave and the first CMUT 197 and the second CMUT 196 are used for transmission and reception of ultrasound waves may be provided.

Thus, the size of an element used for transmission and reception increases, greater ultrasound waves may be transmitted, and the reception sensitivity may be increased. Therefore, high-precision transmission and reception signals may be obtained. In this embodiment, the center frequency of an ultrasound wave used for transmission and reception is set to be higher than the center frequency of an ultrasound wave reception signal and used. Thus, an image in which the resolution of a photoacoustic imaging image is closer to the resolution of an ultrasound imaging image and the ultrasound imaging image is more precise may be obtained.

Twelfth Exemplary Embodiment

The ultrasound probe described in any of the first to eighth embodiments may be used for reception of photoacoustic waves (ultrasound waves) utilizing photoacoustic effects, and may be applied to a test object information acquisition device including the ultrasound probe.

Figure 14:
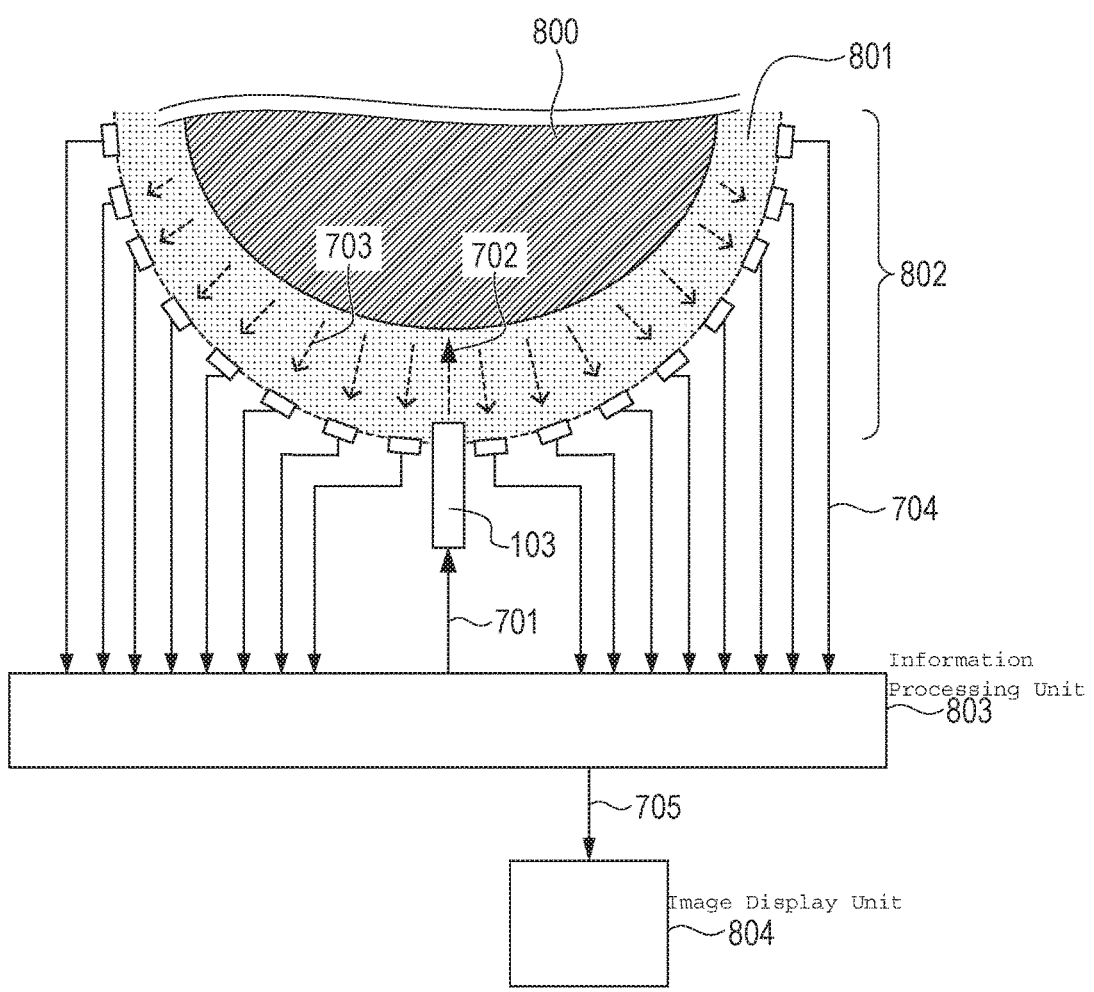
FIG. 14 is a schematic diagram explaining a test object information acquisition device according to an embodiment of the present disclosure.

Operation of a test object information acquisition device according to this embodiment will be specifically described with reference to FIG. 14. First, by causing the light source 103 to generate light 702 (pulse light) based on a light emission instruction signal 701, a measurement object 800 is irradiated with the light 702. Photoacoustic waves (ultrasound waves) 703 are generated at the measurement object 800 by irradiation with the light 702, and the ultrasound waves 703 are received at a plurality of CMUTs 802 included in the ultrasound probe. Information of the size, shape, and time of a reception signal is transmitted as ultrasound wave reception signals 704 to an information processing unit 803. Meanwhile, information (light emission information) of the size, shape, and time of the light 703 generated at the light source 103 is stored in the information processing unit 803 for photoacoustic signals. The information processing unit 803 for photoacoustic signals generates an image signal of the measurement object 800 based on the ultrasound wave reception signals 704 and the light emission information, and outputs the image signal as image information 705 of the test object by the photoacoustic signals. An image display unit 804 displays the test object 800 as an image based on the image information 705 of the test object by the photoacoustic signals.

The ultrasound probe according to this embodiment has a characteristic of being able to receive ultrasound waves over a wide frequency range, and is thus able to receive a large amount of information from the ultrasound waves. Therefore, a high-quality image may be generated.

Thirteenth Exemplary Embodiment

In this embodiment, any of the ultrasound probes according to the ninth to eleventh embodiments is used for a test object information acquisition device according to the twelfth embodiment.

Figure 15:
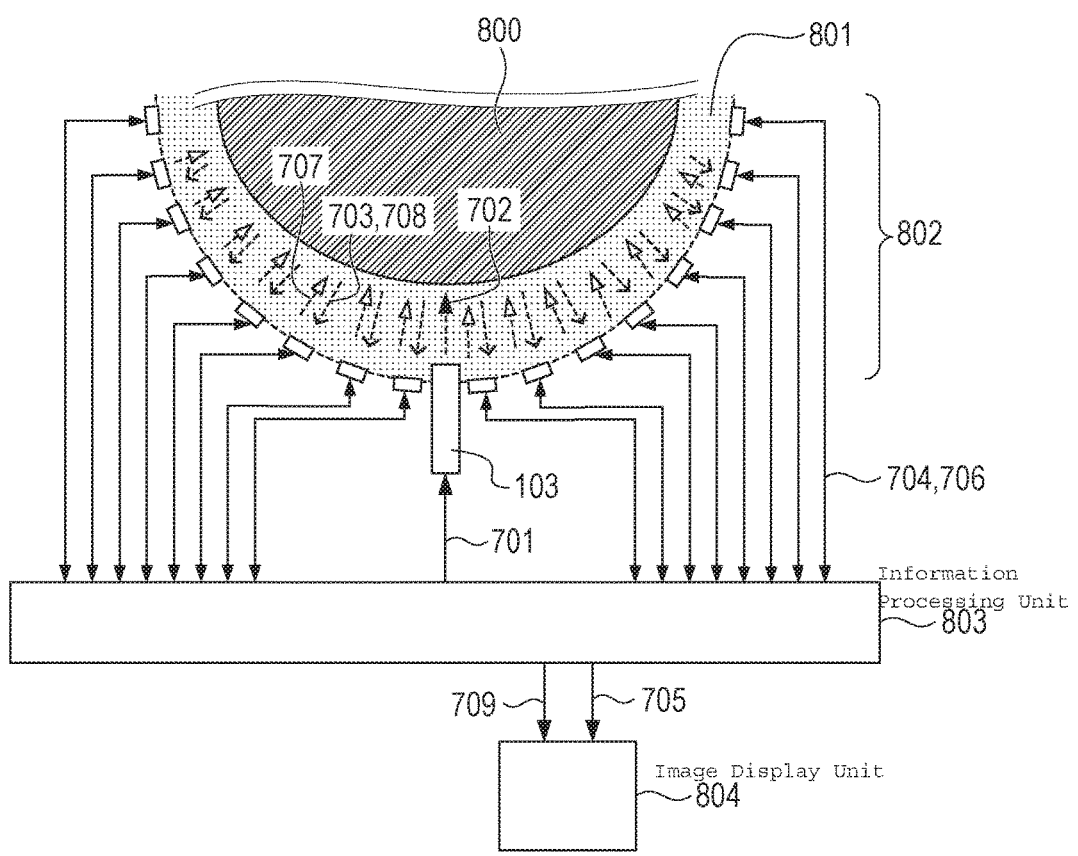
FIG. 15 is a schematic diagram explaining a test object information acquisition device according to an embodiment of the present disclosure.
Figure 16:
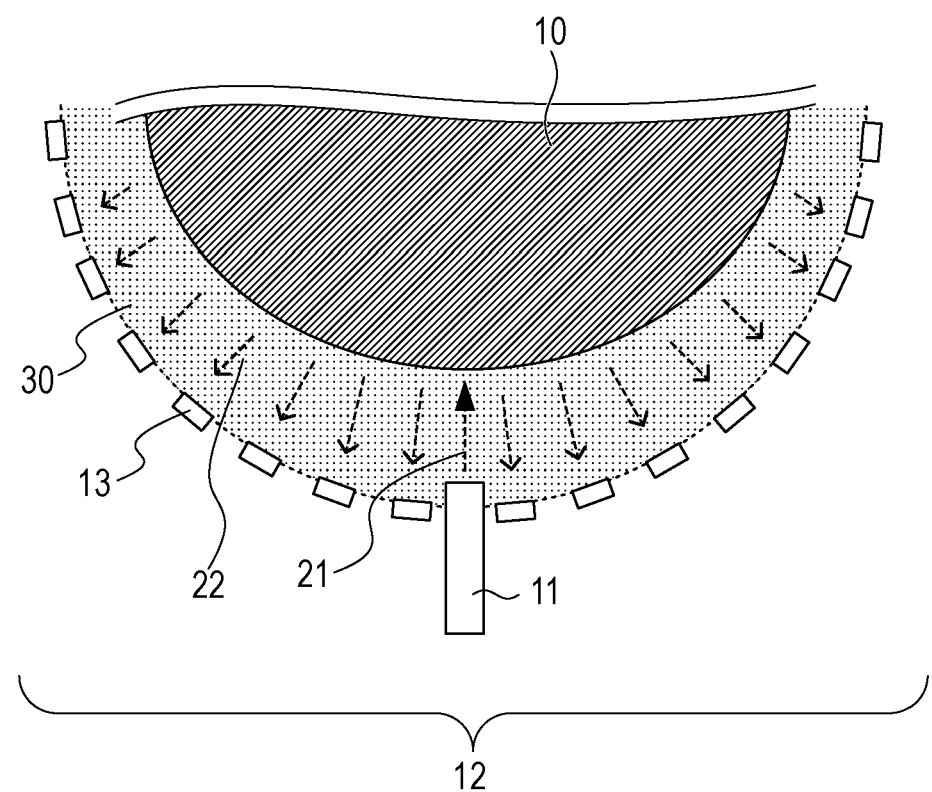
FIG. 16 is a diagram explaining an ultrasound probe of a related art.

FIG. 15 is a schematic diagram of an image forming device according to this embodiment. In FIG. 15, 706 denotes ultrasound wave transmission and reception signals, 707 denotes transmitted ultrasound waves, 708 denotes reflected ultrasound waves, and 709 denotes image information of the test object by transmission and reception of ultrasound waves.

The image forming device according to this embodiment performs pulse-echo (transmission and reception of ultrasound waves), in addition to reception of ultrasound waves, and forms an image. Since reception of ultrasound waves is the same as the twelfth embodiment, pulse-echo (transmission and reception of ultrasound waves) will be explained here. Ultrasound waves may be expressed as photoacoustic waves. Therefore, the test object information acquisition device may be expressed as a photoacoustic device.

Based on ultrasound wave transmission signals 706, ultrasound waves 706 are output (transmitted) toward the measurement object 800 from the plurality of CMUTs 802. Inside the measurement object 800, due to a difference among the acoustic impedances unique to inherent materials, ultrasound waves are reflected. The reflected ultrasound waves 708 are received by the plurality of CMUTs 802, and information of the size, shape, and time of reception signals is transmitted as the ultrasound wave reception signals 706 to the image information generation device 803. Meanwhile, information of the size, shape, and time of transmission ultrasound waves is stored as ultrasound wave transmission information in the information processing unit 803. The information processing unit 803 generates an image signal of the test object 800 based on the ultrasound wave reception signals 706 and the ultrasound wave transmission information, and outputs the image signal as the image information 709 of the test object for ultrasound wave transmission and reception.

The image display unit 804 displays the test object 800 as an image, based on two types of information, the image information 705 of the test object by photoacoustic signals and the reproduction image information 708 by ultrasound wave transmission and reception. According to this embodiment, reception information of different measurement methods is acquired and an image is formed by using an ultrasound probe with a characteristic of being able to receive ultrasound waves over a wide frequency range. Therefore, an image with a larger amount of information may be acquired and displayed.

In the ultrasound probe according to the present disclosure, electrostatic capacitance type transducers having a characteristic of being able to receive photoacoustic waves (ultrasound waves) over a wide frequency range are provided in a plurality of flat surface parts of an inner wall surface of a supporting member having a curved surface. Therefore, photoacoustic waves (ultrasound waves) over a wide frequency band may be detected with high sensitivity.

While the present disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

This application claims the benefit of International Patent Application No. PCT/JP2014/081520, filed Nov. 28, 2014, which is hereby incorporated by reference herein in its entirety.

The invention claimed is:

1. An ultrasound probe comprising:
   electrostatic capacitance type transducers, each including a vibration film which includes a first electrode and a second electrode which is provided with a space between the vibration film and the second electrode;
   a supporting member that has a curved surface on which a plurality of transducers are provided;
   a reception circuit that receives current output by a change in an electrostatic capacitance between the first electrode and the second electrode, and that converts the current into voltage; and
   wiring configured to electrically connect the transducer and the reception circuit and provided inside the supporting member,
   wherein an inner wall surface of the supporting member includes a plurality of recessed flat surface parts, and the transducers are provided on the recessed flat surface parts with plate-like substrates therebetween, and
   wherein the reception circuit is provided on an opposite side of a side where the transducers are provided and outside the supporting member.

2. The ultrasound probe according to claim 1, wherein perpendicular lines for the plurality of recessed flat surface parts of the supporting member cross each other on an inner side of the supporting member, and normal lines for reception surfaces of the plurality of transducers cross each other.

3. The ultrasound probe according to claim 1, wherein an insulating film which covers the transducers is provided on the inner wall surface of the supporting member.

4. The ultrasound probe according to claim 1, wherein wiring which penetrates through the supporting member is provided.

5. The ultrasound probe according to claim 4, wherein wiring which penetrates through a plate-like substrate and wiring which is arranged on the inner wall surface of the supporting member are connected by a bump which is arranged on a rear face of the plate-like substrate.

6. The ultrasound probe according to claim 1, wherein one transducer from the plurality of transducers and the reception circuit are connected via a flexible print board.

7. The ultrasound probe according to claim 6, wherein the one transducer and the flexible print board are connected via an anisotropic conductive resin.

8. The ultrasound probe according to claim 6, wherein the one transducer and the flexible print board are connected via wiring which penetrates through a plate-like substrate.

9. The ultrasound probe according to claim 1, wherein the reception circuit is provided on a circuit board, and the circuit board is arranged in a direction perpendicular to a depth direction of a hemisphere of the supporting member.

10. The ultrasound probe according to claim 1, wherein the reception circuit is provided on a circuit board, and the circuit board is arranged in a direction parallel to a depth direction of a hemisphere of the supporting member.

11. The ultrasound probe according to claim 1, wherein the ultrasound probe with a hemispherical surface shape is configured by combining a plurality of ultrasound probe units.

12. The ultrasound probe according to claim 1, further comprising adjusting means for adjusting DC voltage to be applied to the first electrode or the second electrode through a voltage-dividing resistor.

13. The ultrasound probe according to claim 1, wherein the second electrode and the reception circuit are connected by a connector.

14. The ultrasound probe according to claim 13, wherein a voltage-dividing resistor is provided between the second electrode and the connector.

15. The ultrasound probe according to claim 1, wherein the plurality of transducers are provided on the plate-like substrates, and wherein at least one of the plurality of transducers is a transducer that is able to receive an ultrasound wave and at least one of the plurality of transducers is a transducer that is able to transmit an ultrasound wave.

16. The ultrasound probe according to claim 1, wherein at least one electrostatic capacitance type transducer that performs transmission and reception of an ultrasound wave is provided on a plate-like substrate.

17. The ultrasound probe according to claim 1,
   wherein the plurality of transducers are provided on the plate-like substrates, and wherein the ultrasound probe further comprises causing a number of transducers to be used for transmitting of ultrasound waves to be different from a number of transducers to be used for reception of ultrasound waves.

18. An ultrasound probe comprising:
   electrostatic capacitance type transducers with each transducer comprising:
      a vibration film which includes a first electrode; and
      a second electrode which is provided with a space between the vibration film and the second electrode; and
   a supporting member that has a curved surface on which a plurality of transducers are provided;
   a reception circuit that receives current output by a change in an electrostatic capacitance between the first electrode and the second electrode and that converts the current into voltage; and
   wiring configured to electrically connect the transducer and the reception circuit and provided inside the supporting member,
   wherein an inner wall surface of the supporting member includes a plurality of recessed flat surface parts, and the transducers are provided on the recessed flat surface parts with plate-like substrates therebetween,
   wherein perpendicular lines for the plurality of recessed flat surface parts of the supporting member cross each other at a single point on an inner side of the supporting member, and normal lines for reception surfaces of the plurality of transducers cross each other at the single point, and
   wherein the reception circuit is provided on an opposite side of a side where the transducers are provided and outside the supporting member.

19. An information acquisition device comprising:
   the ultrasound probe according to claim 1; and
   a light source that applies light to a test object, wherein ultrasound waves which are generated from the test object irradiated by the light source due to photoacoustic effects are received using the ultrasound probe.

20. The ultrasound probe according to claim 1, wherein a portion of the inner wall surface of the supporting member between two recessed flat surface parts is raised relative to a portion of the inner wall surface of the two recessed flat surface parts.

21. The ultrasound probe according to claim 18, wherein a portion of the inner wall surface of the supporting member between two recessed flat surface parts is raised relative to a portion of the inner wall surface of the two recessed flat surface parts.

* * * * *